US008568587B2

(12) United States Patent
Olesik et al.

(10) Patent No.: US 8,568,587 B2
(45) Date of Patent: Oct. 29, 2013

(54) ELECTRO-SPUN FIBERS AND APPLICATIONS THEREFORE

(75) Inventors: Susan V. Olesik, Dublin, OH (US);
Jonathan E. Clark, Nashville, TN (US);
Jeremy K. Steach, Kingsport, TN (US);
Joseph W. Zewe, Marion Center, PA (US)

(73) Assignee: The Ohio State University Research Foundation, Columbus, OH (US)

( * ) Notice: Subject to any disclaimer, the term of this patent is extended or adjusted under 35 U.S.C. 154(b) by 51 days.

(21) Appl. No.: 13/046,552

(22) Filed: Mar. 11, 2011

(65) Prior Publication Data
US 2011/0214487 A1    Sep. 8, 2011

Related U.S. Application Data

(63) Continuation-in-part of application No. PCT/US2009/056685, filed on Sep. 11, 2009.

(60) Provisional application No. 61/096,139, filed on Sep. 11, 2008.

(51) Int. Cl.
*B01D 15/08* (2006.01)

(52) U.S. Cl.
USPC ............... 210/198.2; 210/198.3; 210/502.1; 210/634; 210/635; 210/656; 210/658

(58) Field of Classification Search
USPC ........... 210/634, 635, 656, 658, 198.2, 198.3, 210/502.1; 977/720, 721, 722
See application file for complete search history.

(56) References Cited

U.S. PATENT DOCUMENTS

| 5,431,821 | A | * | 7/1995 | Olesik et al. ................. 210/635 |
| 5,691,054 | A | | 11/1997 | Tennent et al. |
| 6,780,314 | B2 | * | 8/2004 | Jinno et al. ................. 210/198.2 |
| 7,591,883 | B2 | * | 9/2009 | Kameoka et al. ............... 95/273 |
| 7,655,070 | B1 | * | 2/2010 | Dallas et al. ..................... 95/154 |
| 2004/0211724 | A1 | * | 10/2004 | Gibson et al. ................. 210/638 |
| 2006/0159916 | A1 | * | 7/2006 | Dubrow et al. ............... 428/357 |
| 2006/0223947 | A1 | * | 10/2006 | Olesik et al. ............... 525/328.1 |
| 2007/0190880 | A1 | * | 8/2007 | Dubrow et al. ............... 442/181 |
| 2007/0196401 | A1 | * | 8/2007 | Naruse et al. ................. 424/401 |

FOREIGN PATENT DOCUMENTS

| CN | 1405560 | 3/2003 |
| EP | 1203953 | 5/2002 |
| WO | 2005075048 | 8/2005 |

OTHER PUBLICATIONS

Clark, Jonathan E., Technique for Ultrathin Layer Chromatography Using an Electrospun, Nanofibrous Stationary Phase, Anal. Chem. 2009, 81, 4121-29.
Clark, Jonathan E., Electrospun Glassy Carbon UTLC Devices, submitted to The Journal of Chromatography A, Anal. Chem. 2009, 81, 4121-4129.

(Continued)

*Primary Examiner* — Ernest G Therkorn
(74) *Attorney, Agent, or Firm* — Standley Law Group LLP

(57) ABSTRACT

A supported nanofiber medium useful for segregating chemical species is provided by selecting a polymer, selecting a substrate; and electrospinning the polymer to form a nanofiber medium on the supporting substrate. When the substrate is a planar surface, the nanofiber medium will be a mat suitable for conducting chromatographic separation. When the substrate is a filament, the nanofiber medium is an annular mat suitable for solid phase microextraction. The nanofiber media formed may be selectively cross-linked and at least partially carbonized to carbon nanofibers. The nanofiber medium is supported on the substrate without the use of binder material.

14 Claims, 21 Drawing Sheets

(56) References Cited

OTHER PUBLICATIONS

Steach, Jeremy, The Doctoral Dissertation of Jeremy Steach entitled: The Development of Novel Phases with Photoresist for Capillary Electrophoresis, Capillary Electrochromatography, and Solid-Phase Microextraction, The Ohio State University, 2008.

Saito, Yoshihiro, Fiber-in-tube solid-phase microextraction: a fibrous rigid-rod heterocyclic polymer as the extraction medium, Fresenius J. Anal. Chem. 2000, 368: 641-643.

Farson, Dave F., Femtosecond laser micromachining of dielectric materials for biomedical applications, 2008 J. Micromech. Microeng. 18 035020 (9pp).

Anariba, F., Strong Effects of Molecular Structure on Electron Transport in Carbon/molecule/Copper Electronic Junctions, J. Phys. Chem. B, 2005; 109(22); 11163-11172.

Abstract of RU 2289588.

Abstract of RU 2105972.

\* cited by examiner

US 8,568,587 B2

ELECTRO-SPUN FIBERS AND APPLICATIONS THEREFORE

CROSS-REFERENCE TO RELATED APPLICATIONS

This application is a continuation-in-part of and claims priority to PCT/US2009/056685, filed Sep. 11, 2009, which claims priority to U.S. Provisional Patent Application No. 61/096,139, filed Sep. 11, 2008, both of which are incorporated by reference as if fully recited herein.

STATEMENT REGARDING FEDERALLY-SPONSORED R & D

The present invention was made with Government support under at least one of the following grants awarded by the National Science Foundation: 0616709, EEC-04-25626, and CHE-04-40499. The United States Government may have certain rights to this invention under 35 U.S.C. §200 et seq.

TECHNICAL FIELD

The disclosed embodiments are in the field of producing fibers by an electrospinning process and in applying the fibers so produced to industrially useful applications. In a first application, the fiber is integrated into a stationary phase of a thin-layer chromatography system. In a second application, the fiber is integrated into a system for solid phase microextraction.

BACKGROUND

Thin layer chromatography (TLC) is a technique known in chemistry to separate chemical species, and has a wide range of uses in the fields of pharmaceuticals, water quality analysis and organic synthesis. A stationary phase provides a tortuous flow path, and the thin layer is often formed from a material such as silica gel, alumina or cellulose, with the material selected for the porosity provided and its inert chemical nature, relative to the components of the liquid phase. A liquid phase consists of a mixture of compounds to be separated, dissolved in an appropriate solvent. The liquid phase is placed on the thin layer plate and is drawn up the plate by capillary action, with the mobility of the compounds in the mixture determined by the interactions of the analytes with the stationary phase.

Known impediments to wider use of the TLC technique include the cost and difficulty of fabricating the stationary phase, as well as the brittleness of it. A further impediment is the minimum size of the diameter and thickness available for a stationary phase plate fabricated from the conventional materials.

Solid phase microextraction (SPME) is an extraction technique that was developed as a fast method to analyze volatile and semivolatile compounds. SPME offers an inexpensive and solvent-free extraction method that is a viable alternative to liquid-liquid extractions and solid phase extractions. This technique was developed by Berladi and Pawliszyn in 1989.

A typical apparatus used in SPME comprises a silica rod or platinum wire that is coated with a specific extraction medium. SPME fibers often have a length of about 1 cm, and the desired thickness of the extraction medium ranges from a monolayer to about 100 µm. The coated fibers are used by placing the fiber in contact with the sample matrix, a bulk fluid or its surrounding headspace. The fibers can be used to analyze samples from the liquid phase, gaseous, or solid matrices. The samples are measured by direct exposure of the fiber to the bulk fluid or its surrounding headspace.

By developing a fiber coating with different functionalities, SPME fibers can be chosen for the specific analyte(s) of interest. This allows the performance of SPME to be optimized where only the analytes of interest are analyzed rather than having matrix effects interfering in the extraction. By decreasing matrix effects, the detection limit of the analytes can be lowered.

As described, the separation techniques of TLC and SPME have known impediments.

SUMMARY OF THE INVENTIVE CONCEPT

These and other impediments of the prior art separation techniques are solved at least in part by a method for manufacturing a supported nanofiber medium useful for segregating chemical species, comprising the steps of: selecting a polymer; selecting a substrate; and electrospinning the polymer, forming a nanofiber medium on the supporting substrate.

Some aspects of the method provide a device for analytically separating chemical species, comprising a substrate and a polymeric nanofiber medium formed on at least one surface of the substrate, where the substrate is a planar surface; and the nanofiber medium comprises a mat suitable for conducting chromatographic separation.

Other aspects provide a device where the substrate is a filament; and the nanofiber medium comprises an annular mat suitable for solid phase microextraction.

Yet further aspects of the method, by providing the supported nanofiber media, provide an improved method for segregating at least two chemical species.

BRIEF DESCRIPTION OF THE DRAWINGS

In addition to the features mentioned above, other aspects of the inventive concept will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

To the extent that they compliment the specification and are enabling of the disclosed embodiments, the following publications are incorporated by reference as if recited in their entirety herein: Clark, Jonathan E., Technique for Ultrathin Layer Chromatography Using an Electrospun, Nanofibrous Stationary Phase, Anal. Chem. 2009, 81, 4121-29; Clark, Jonathan E., a manuscript entitled: Electrospun Glassy Carbon UTLC Devices, submitted to The Journal of Chromatography A; and The Doctoral Dissertation of Jeremy Steach entitled: The Development of Novel Phases with Photoresist for Capillary Electrophoresis, Capillary Electrochromatography, and Solid-Phase Microextraction, available at the Ohio State University.

Electrospinning Fibers

Referring first to the formation of the fibers that are useful in the TLC and SPME applications, among other applications, electrospinning involves placing a high electric field between a polymer solution and a conductive collector. This collector may be comprised of many different materials such as metals, conductive polymers or the like, and may take the form of a plate, a film, a filament, a rod etc. When an electric field strong enough to overcome the surface tension of the droplet is provided, a Taylor cone is formed. Following the creation of the Taylor cone, fibers are ejected toward the conductive collector. With this technique, many different polymers and polymer blends can be used to generate and spin fibers with various chemical compositions and to fabricate mats comprising the fibers without the aid of binders.

There are advantages of electrospinning a photoresist material, such as the high contrast epoxy based photoresist available for Microchem, Corp., of Newton, Mass., under the designation SU-8 2100, referred to hereinafter as "SU-8." By using SU-8 photoresist to electrospin micro/nanofibers, the nonwoven fiber mats can easily be patterned after the fibers are electrospun allowing greater flexibility in patterning. Patterning of a photoresist polymer such as SU-8 is generally accomplished by selectively exposing sections of the fibers to UV light and then removing uncrosslinked polymer from the substrate.

Figure 1:
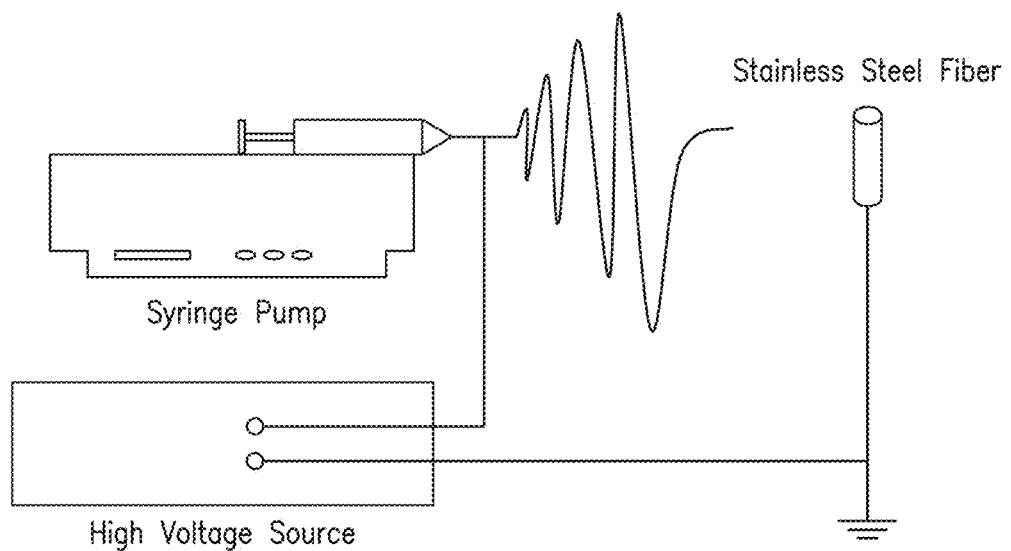
FIG. 1 is a schematic of an electrospinning apparatus used.

An apparatus used for electrospinning is shown in FIG. 1. SU-8 solutions including 100%, 75, 70, 50, 25 and 0% (v/v) were prepared using commercially available cyclopentanone. A Spellman CZE 1000R high voltage power supply was used to supply voltages from 5 to 15 kV. A Harvard Model 33 dual syringe pump was used to control the flow rate of the SU-8 solutions. The flow rates were varied from 0 to 2 mL/min. Cleaved silicon pieces from a silicon wafer were used as the collector for the fibers. Electrospinning experiments were performed while varying the following parameters: SU-8/cylcopentanone (v/v) concentrations, voltage, flow rate, and distance to determine the optimum parameters for production of fibers. After each experiment, the fibers were exposed to a UV light to crosslink the SU-8 fibers.

Samples were prepared in sets of two by this electrospinning method. After electrospinning, both samples were exposed to UV radiation for approximately five minutes. One sample was then kept in a vial and the other was placed in a quartz tube furnace for pyrolysis. Once the sample was placed in the furnace, a forming gas mixture (95% N2 and 5% H2) was flowed through the quartz tube to remove any oxygen. The furnace was ramped at 1° C./min to a final temperature of 800° C.

Forming gas flowed continuously for the duration of the pyrolysis. The final temperature was held for a minimum of 5 hours before the pyrolysis was stopped. After the furnace was turned off, the sample was allowed to cool to room temperature (25° C.) under a constant flow of forming gas.

To pattern the fibers, the SU-8 was first electrospun onto the silicon collector as described above. The pattern was created by using a lithographic mask or by printing the desired shape onto a transparency. The lithographic mask or transparency was placed onto the fibers and then the fibers were exposed to the UV source. After exposing the fiber samples to UV radiation, SU-8 developer was used to remove the fibers that were not crosslinked.

All electron microscopy images of the electrospun fibers were taken using a Hitachi S-4300 scanning electron microscope. Each SU-8 sample was sputter coated with gold prior to obtaining the images, while the pyrolyzed fiber samples were not coated to obtain images.

Figure 2:
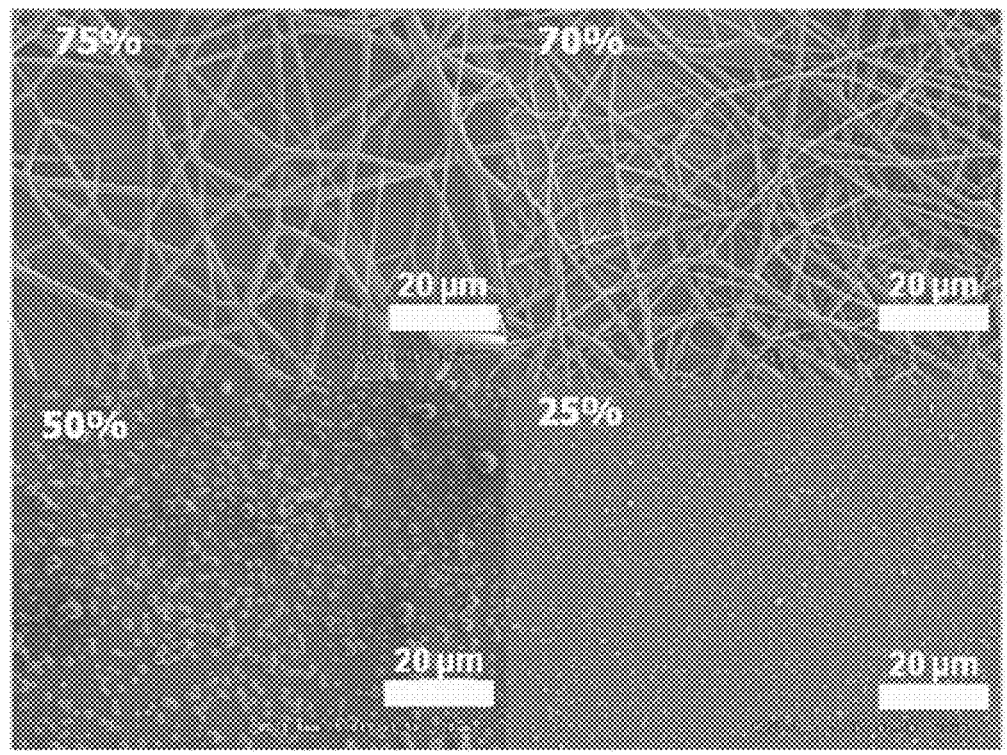
FIG. 2 is a set of scanning electron microscope (SEM) images showing products produced when varying the concentration of SU-8 in the solution.

After the initial experiments, several dilutions between 75% and 25% were attempted to further optimize the conditions for fiber production. It was found that 75% and 70% SU-8 solutions resulted in fibers for the various voltages (5-15 kV), distances (5-29 cm), and flow rates (0-0.2 mL/min) examined. The other concentrations did not produce fibers or produced fibers along with polymer beads. As shown in FIG. 2, the 50% and 25% SU-8 concentrations yielded beads at the same parameters as 75% and 70% SU8 concentrations. Both 100% and 0% SU-8 concentrations resulted in no fibers or particles on the collector. The SEM images shown in FIG. 2 were obtained for the various % SU-8 concentrations at the same electrospinning parameters to determine the effective concentration range to generate fibers.

The effect of distance on the fibers produced was also measured for both the 70 and 75% solutions. Fibers were produced effectively at distances from 10 cm to 29 cm. The 75% solution yielded larger fibers than the 70% for each distance, ranging from 1.08 µm at 10 cm to 830 nm at 29 cm. The 70% yielded average fiber sizes ranging from 770 nm to 530 nm on average.

To test the effect of voltage on both solutions, the distance was set to 10 cm and the flow rate was kept constant at 0.02 mL/min. For both 75% and 70% concentrations, the fibers decreased in average diameter at certain voltages. For the 70% solution, voltages below 9 kV were tested and did not provide any smaller diameter fibers but actually the fiber size increased slightly. At 5 kV, the 70% electrospun fibers were measured to be 830 nm±340 nm compared to 490 nm±140 nm for 9 kV. For the 75% SU-8 dilution, the average fiber diameters were measured displayed an even larger decrease in size when electrospun at 9 kV. The average fiber diameter decreased from 1.08 µm (10 kV) to 301 nm (9 kV). Lower voltages were tested for the 75% concentration, and the average fiber diameter increased compared to 9 kV. For example, at a voltage of 5 kV, the average fiber diameter was 560 nm±300 nm which is a slight increase in fiber diameter at the chosen electrospinning parameters. So, a voltage of 9 kV was chosen to be the best voltage for both concentrations under the electrospinning parameters investigated.

Figure 3:
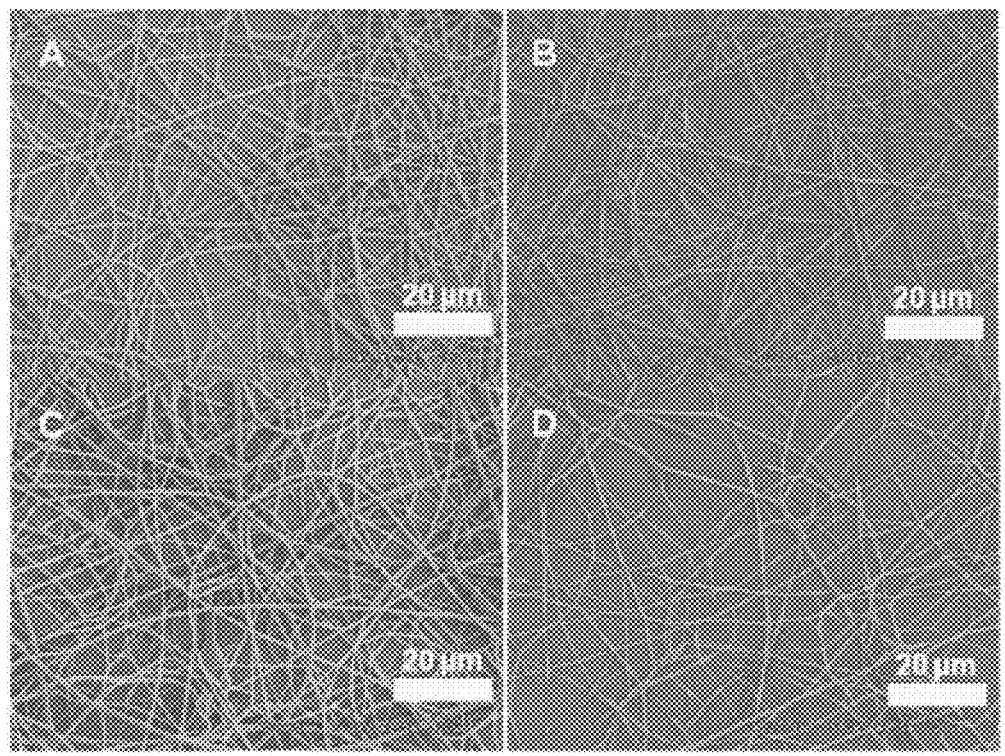
FIG. 3 is a set of SEM images showing pyrolyzed and unpyrolyzed fibers obtained.
Figure 4:
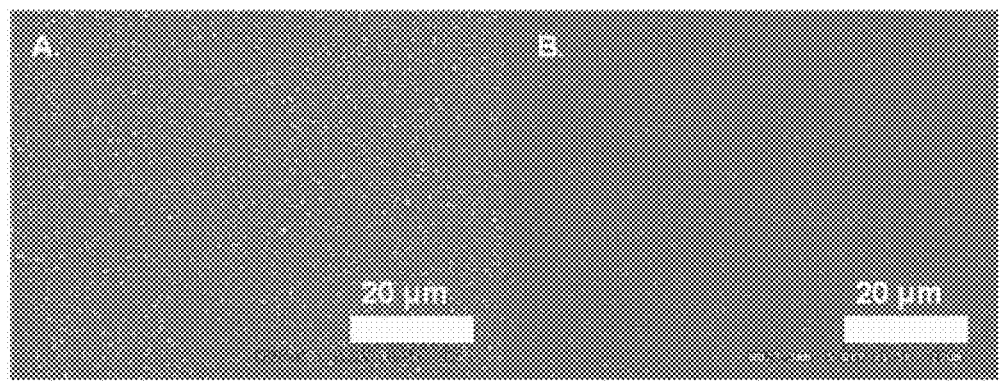
FIG. 4 is a set of SEM images showing pyrolyzed and unpyrolyzed beads obtained.

Pyrolysis of electrospun SU-8 fibers generates carbon fibers. FIG. 3 shows the pyrolyzed fibers produced from both the 75% and 70% SU8 solutions. Samples were pyrolyzed using substantially the same method described above. The fiber diameter decreased after pyrolysis but still maintained the same fiber structure that existed prior to heating.

Figure 5:
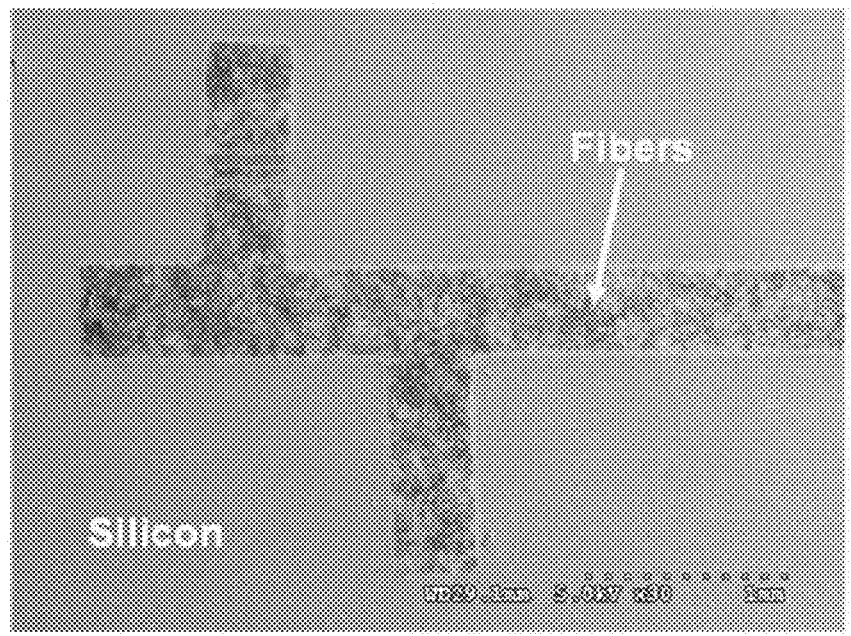
FIG. 5 is an SEM image of typical UV patterned electrospun fibers.

An advantage to electrospinning a polymer that can be selectively cross-linked, such as SU-8 photoresist, is that electrospun fiber patterns can be generated. FIG. 5 is an SEM image of a pattern generated by exposing portions of the fiber mat to UV light after electrospinning In conventional electrospinning, the fibers are typically patterned by using different collectors. Though these patterns generate aligned or oriented fibers, most of them do not provide a method to pattern the nonwoven fibers into several different patterns. The advantage of being able to pattern fibers via UV radiation is that UV photolithography can be used to easily generate any fiber pattern. The ease of creating a patterned mat of SU-8 fibers can lead to many application possibilities.

From this, it is shown that an optimized process exists to generate electrospun fibers from an SU-8 2100 negative photoresist. The electrospun SU-8 fibers generated had diameters ranging from 300 nm to 1 µm which are dependent upon the set of parameters used. The fibers may be easily patterned by UV and then converted to carbon fibers via pyrolysis. The fiber structure is maintained after pyrolysis. By utilizing the advantage of patterning the fibers after electrospinning, many applications ranging from microfluidics, sensors to micro/nanoelectronics can potentially be achieved.

Solid Phase Microextraction

In one embodiment, electrospinning is employed to coat a substrate, such as a stainless steel wire or other conductive filament or surface, with a mat of fibers. This electrospinning of polymeric fibers provides the capability to create micro/nanofibers for chemical extraction and chromatography through an inexpensive and simple method.

The parameters for the optimization of electrospinning SU-8 are described above. SPME fibers may also be pyrolyzed to yield carbon-based fiber coated SPME wires. The extraction characteristics of the SU-8 and pyrolyzed electrospun-coated wires were investigated for nonpolar and polar compounds under headspace extraction conditions.

Benzene (99.9%), toluene (99.8%), ethylbenzene (99.8%), o-xylene (98%), phenol, 4-chlorophenol and 4-nitrophenol were used for extractions. Dichloromethane was used to prepare the solutions for benzene, toluene, ethylbenzene, and o-xylene, while HPLC methanol was used to prepare the phenolic solutions.

For comparison, commercially available SPME fibers were purchased from Supelco. The fibers chosen for comparative analysis of nonpolar compounds were an 100-µm polydimethylsiloxane (PDMS) and a Stableflex 65-polydimethylsiloxane/divinylbenzene (PDMS/DVB). To compare the electrospun fiber coated wires for the extraction of phenols; an 85-µm polyacrylate (PA) commercial fiber was used.

The 75% SU-8 2100/cyclopentanone electrospinning solution was prepared as described above. Stainless steel wires were used as the collector for the electrospun fibers. The wires had a diameter of about 127 µm and were commercially available from Small Parts (Miami Lakes, Fla.).

The stainless steel wires were cut into 1.5 cm lengths and previously determined parameters to electrospin a 75% SU-8 2100 solution were used to generate the fibers. The parameters for electrospinning were: voltage of 9 kV, a flow rate of 0.02 mL/min, and a distance of 10 cm. The fibers were electrospun for 30 seconds to create the fiber coating on the stainless steel wire. After electrospinning onto the stainless steel fiber, the fibers were then exposed to a UV light to crosslink the SU-8 fibers.

Utilizing the previously described pyrolysis technique, temperatures of 400, 600, and 800° C. were chosen for production of carbon fibers. The electrospun fiber-coated wires were then transferred to the inlet on the gas chromatograph (GC). The coated wires were held in the inlet for a minimum of 30 minutes or until a steady baseline was achieved.

Extraction time profiles were initially determined by using a mixture of benzene, toluene, ethylbenzene, and o-xylene (BTEX). A 40 ppm BTEX solution was prepared by spiking 25 mL of nanopure water with a 10000 ppm BTEX solution in dichloromethane. After 20 minutes of stirring, the fiber was exposed to the headspace for a set of selected extraction times (0 to 90 minutes) to determine the extraction time profile.

A 10000 ppm BTEX solution was prepared in dichloromethane and used to spike 25 mL of water to a concentration of 40 ppm. An extraction time of 60 minutes was chosen to compare the extraction efficiency of the electrospun fiber-coated wires to commercial fibers.

The extraction time profiles for the phenolic compounds were determined by using a mixture of phenol, 4-chlorophenol, and 4-nitrophenol. A 100 ppm solution of the above phenolic compounds was prepared in HPLC methanol. To perform the extractions, the pH of the nanopure water was lowered to ~1 by the addition of concentrated hydrochloric acid, while sodium chloride (NaCl) was added to the water until saturated. This solution was spiked with the 100 ppm phenolic mixture to give a concentration of 0.4 ppm.

To compare the extraction efficiency of each fiber, a 100 ppm phenolic solution was used. A time of 60 minutes was chosen as the extraction time to compare the electrospun fiber-coated wires to the PA commercial SPME fiber. For analysis of the extraction efficiency, the inlet temperature was 320° C. for the electrospun-coated fibers and the inlet temperature for the PA fiber was held at 280° C. All other chromatographic parameters were kept the same.

By coating the stainless steel wire with electrospun fibers, a porous and high surface area coating is provided for solid-phase microextraction. The nonwoven mat of electrospun fibers was formed around the stainless steel wire collector. Electrospinning times can be altered to yield different fiber coating thicknesses and or density on the stainless steel wire for SPME.

Figure 6:
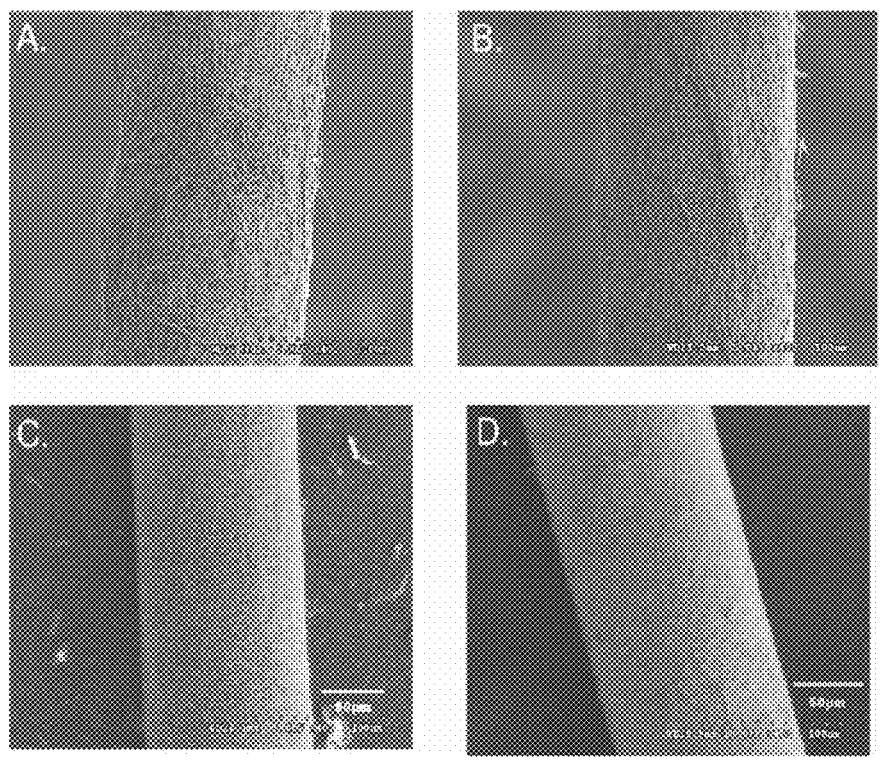
FIG. 6 is a set of SEM images of the electrospun SPME fibers, unprocessed and after processing at various temperatures, A: unpyrolyzed, B: 400° C., C: 600° C., D: 800° C.
Figure 7:
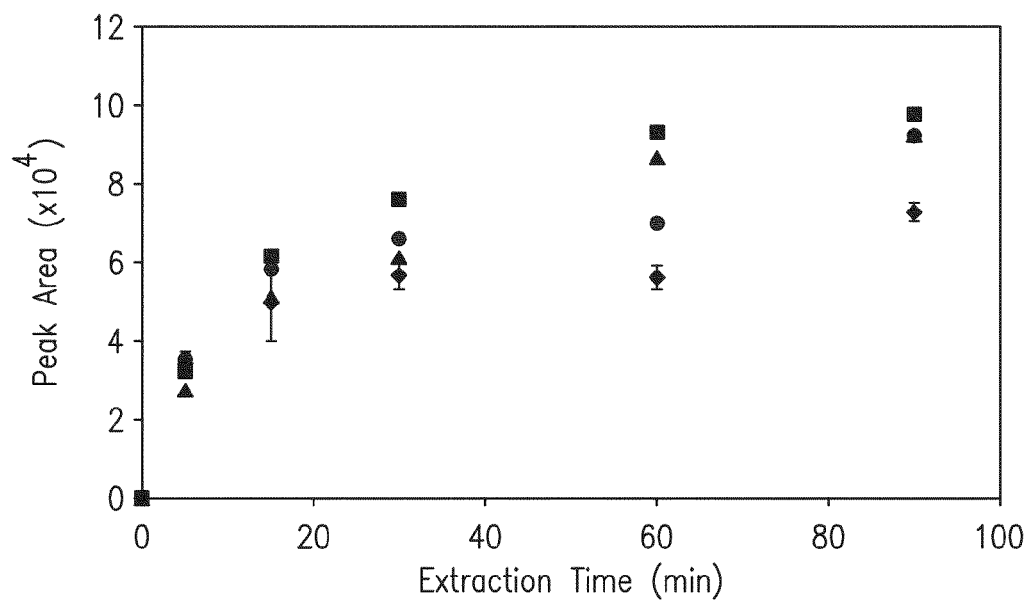
FIG. 7 is an extraction time profile for benzenoid compounds using an SU-8 electrospun fiber-coated SPME wire.
Figure 8:
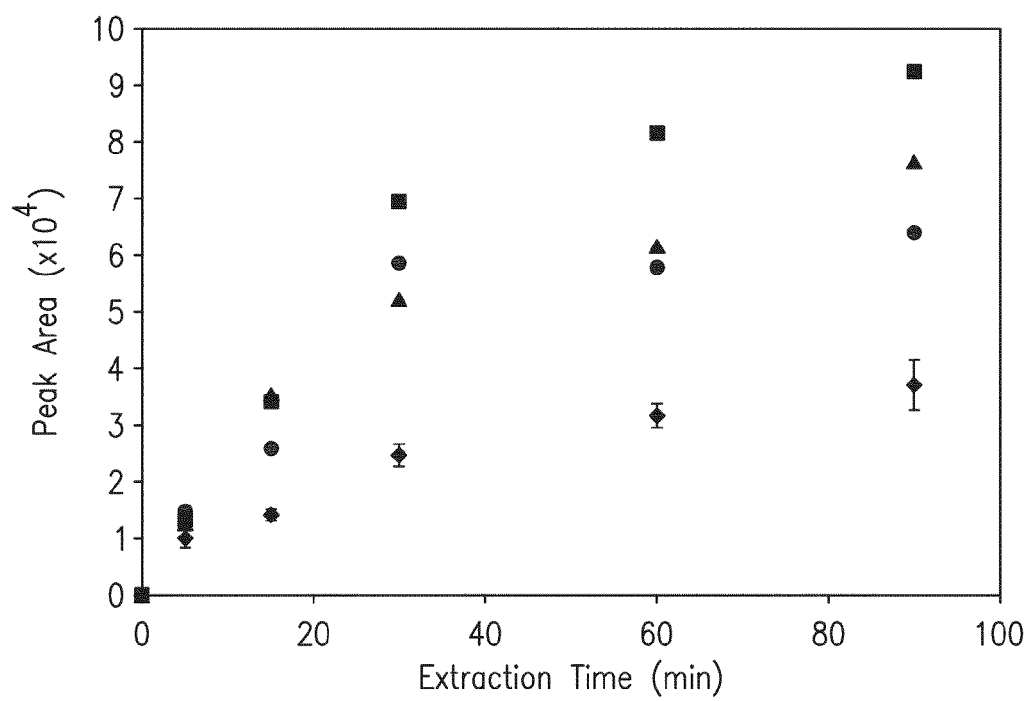
FIG. 8 is an extraction time profile for benzenoid compounds using an electrospun fiber-coated SPME wire processed at 400° C.
Figure 9:
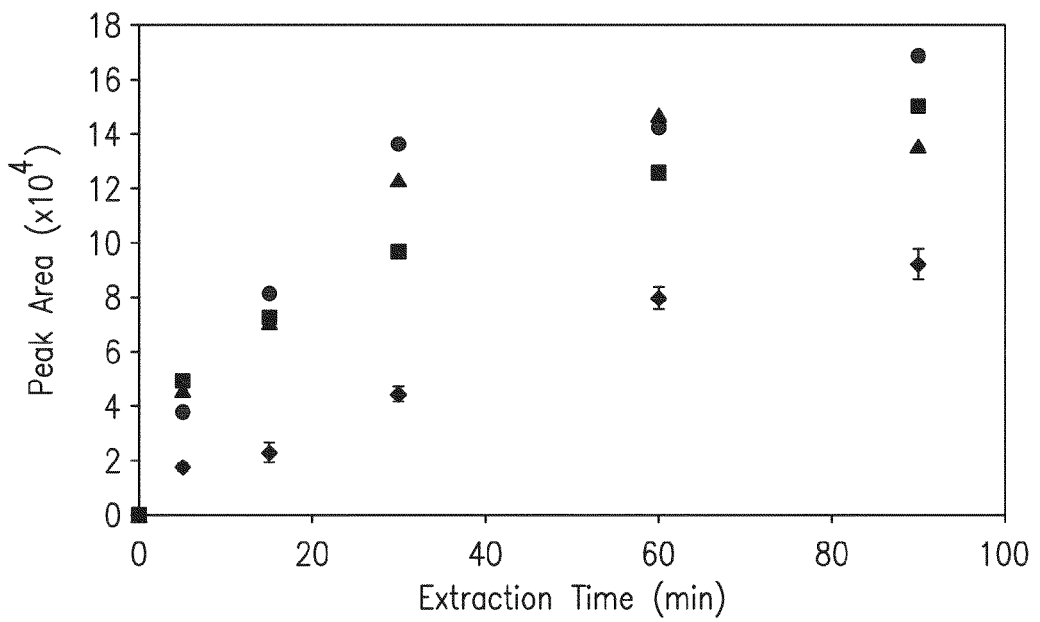
FIG. 9 is an extraction time profile for benzenoid compounds using an electrospun fiber-coated SPME wire processed at 600° C.
Figure 10:
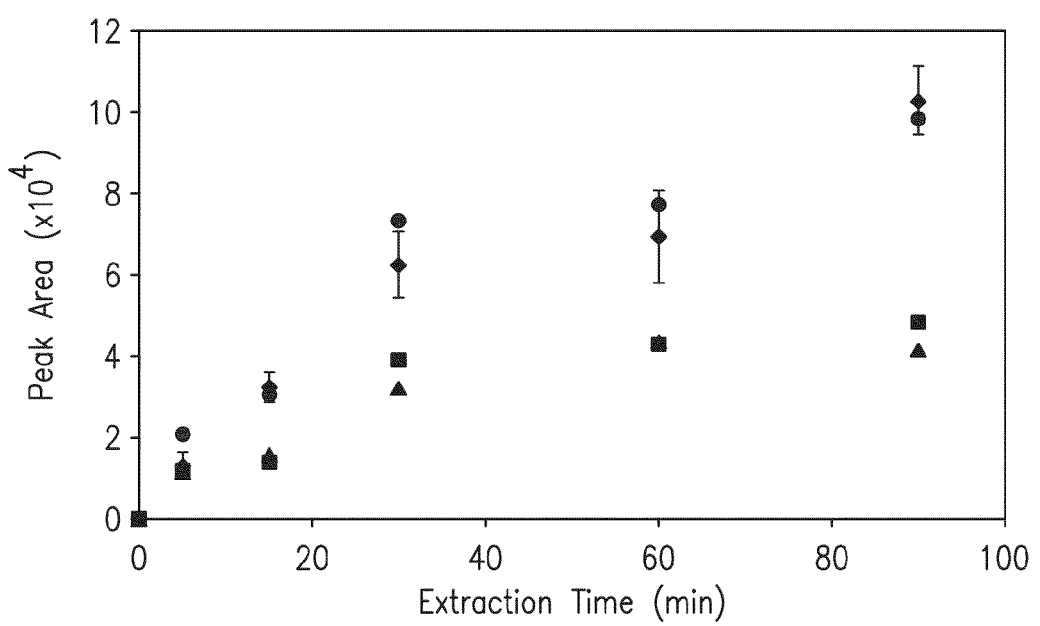
FIG. 10 is an extraction time profile for benzenoid compounds using an electrospun fiber-coated SPME wire processed at 800° C.

FIG. 6 shows SEM images of electrospun SU-8 fibers on a stainless steel wire, where the fibers were electrospun for 30 seconds. Also, FIG. 6 shows the electrospun fiber-coated wires after being processed at the different temperatures (400, 600, and 800° C.). The thickness of each fiber-coated wire was measured by SEM and shown in the following table, where it is shown that the fiber coating thickness decreased as the processing temperature increased.

| Fiber | Coating thickness (μm) |
| --- | --- |
| SU-8 2100 | 18.8 ± 2.3 |
| 400° C. | 11.4 ± 1.0 |
| 600° C. | 6.2 ± 0.7 |
| 800 C. | 3.7 ± 0.2 |

Pyrolysis of electrospun SU-8-coated wires is a way to generate a carbon fiber-coated surface for SPME. Just as in the previous examples, in order to maintain the fiber structure through pyrolysis, the samples must be cross-linked prior to pyrolysis.

Figure 12:
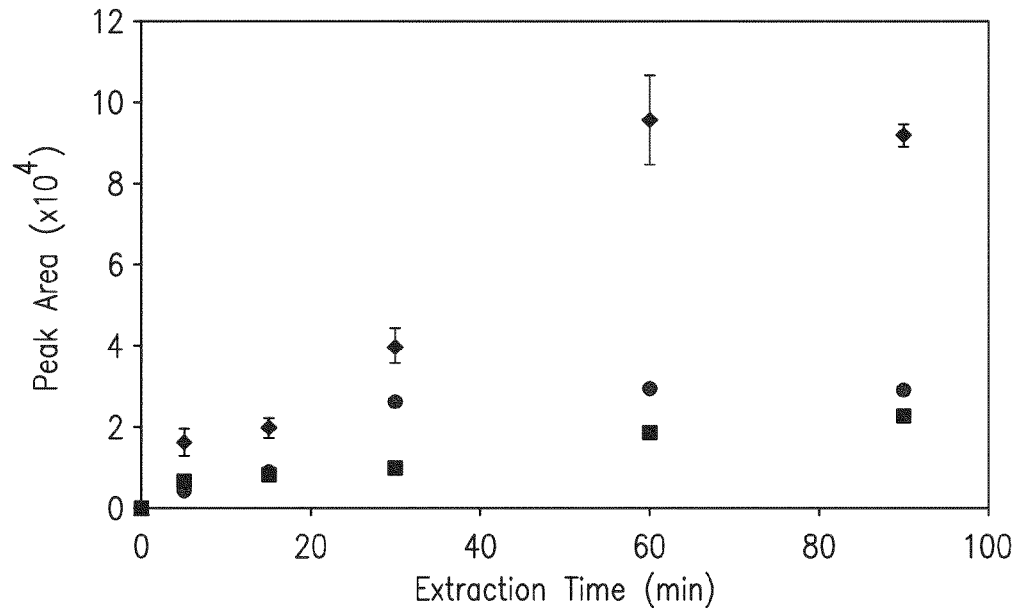
FIG. 12 is an extraction time profile for phenolic compounds using an SU8 electrospun fiber-coated SPME wire.

The extraction capability of the electrospun-coated SPME fibers was first examined with a mixture of benzene, toluene, ethylbenzene, and o-xylene (BTEX). FIG. 12 shows the extraction data obtained for the SU-8 electrospun fiber-coated wire. This fiber-coated wire was not pyrolyzed but only conditioned in the inlet at a temperature of 300° C.

Figure 13:
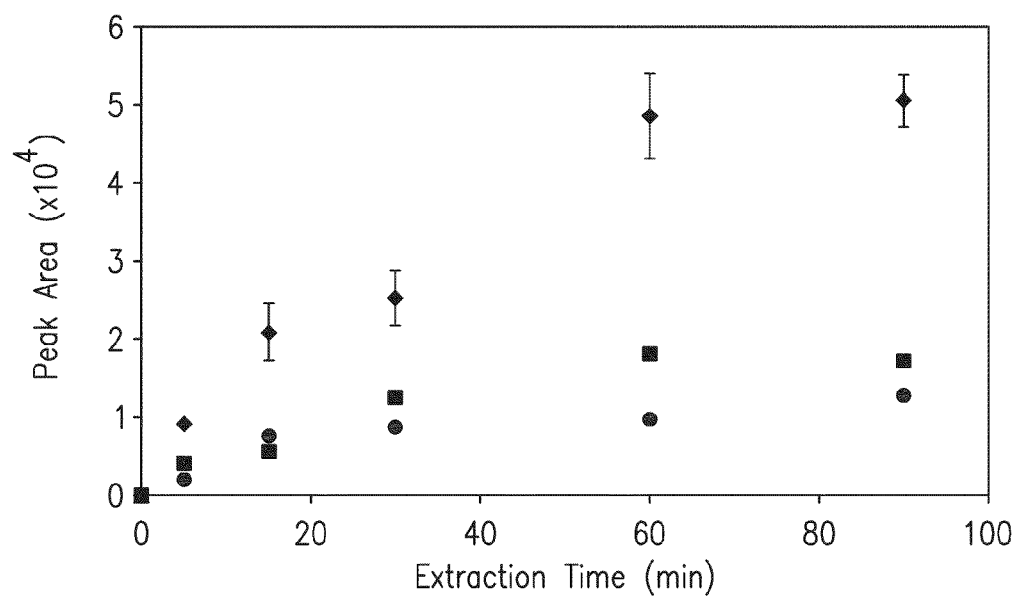
FIG. 13 is an extraction time profile for phenolic compounds using an electrospun fiber-coated SPME wire processed at 400° C.
Figure 14:
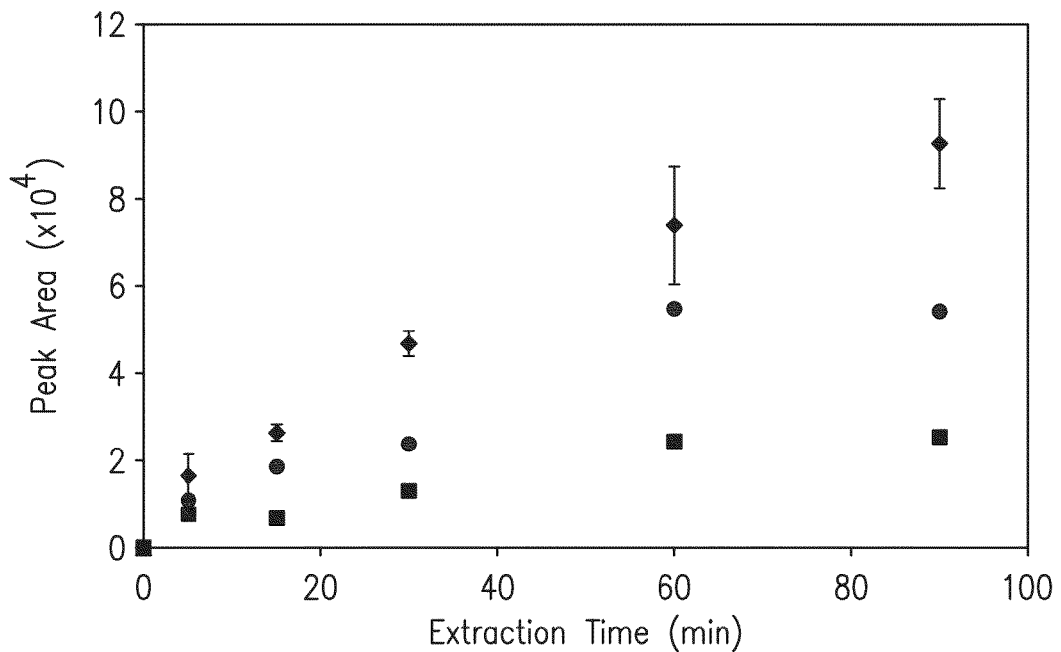
FIG. 14 is an extraction time profile for benzenoid compounds using an electrospun fiber-coated SPME wire processed at 600° C.
Figure 15:
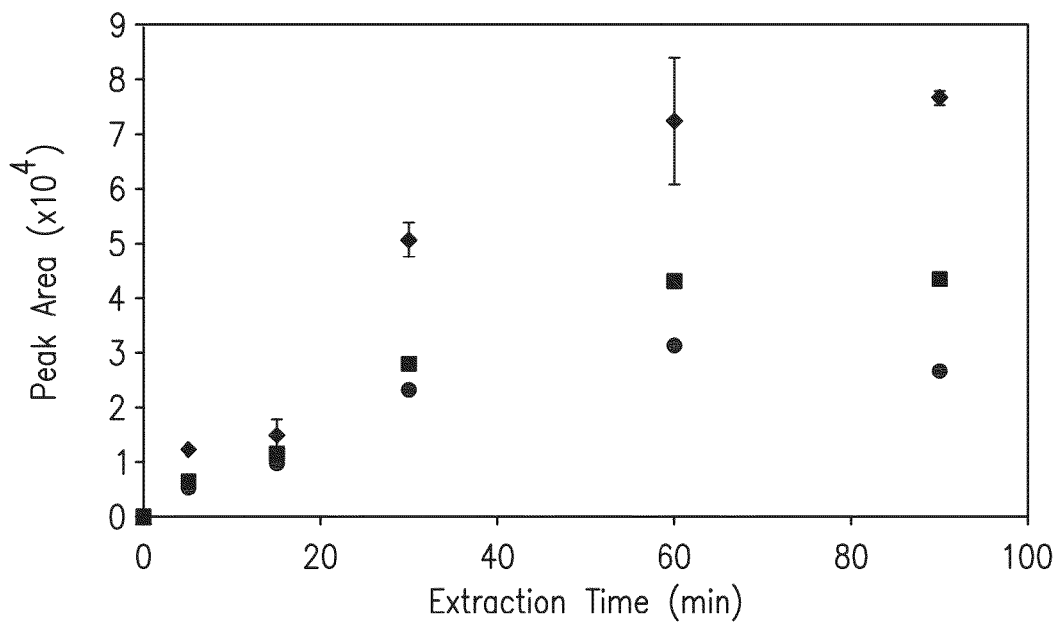
FIG. 15 is an extraction time profile for benzenoid compounds using an electrospun fiber-coated SPME wire processed at 800° C.
Figure 16:
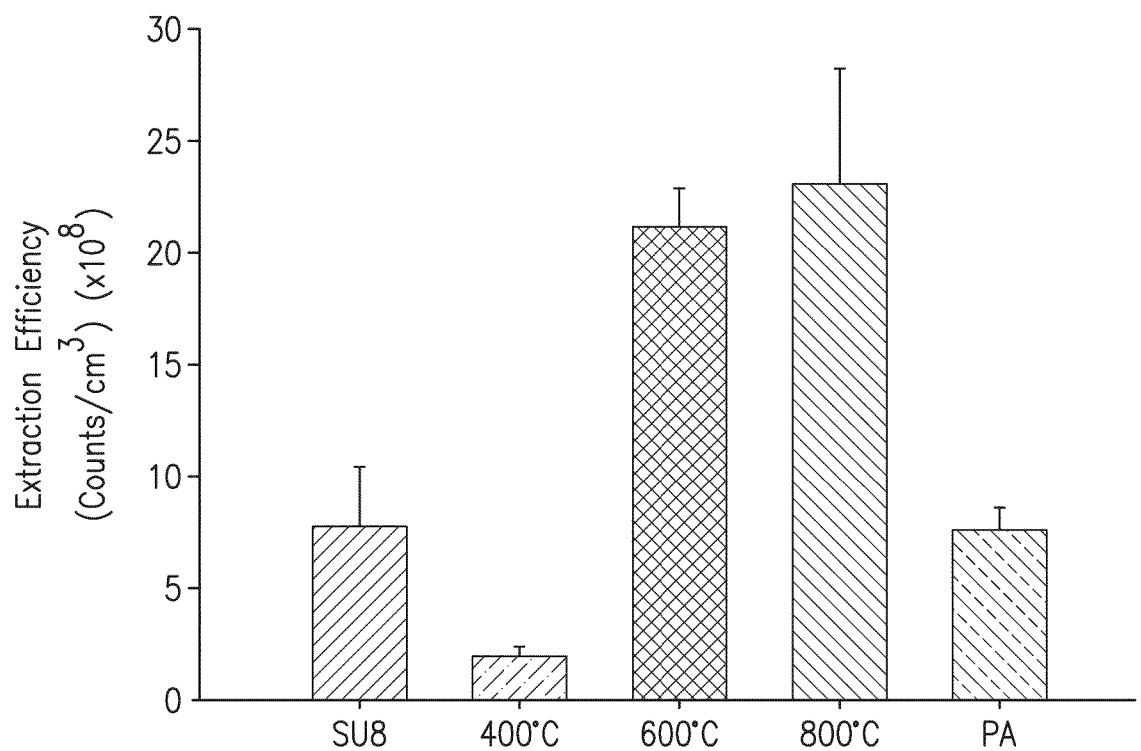
FIG. 16 is an extraction efficiency plot for 4-nitrophenol using various SPME systems.

FIG. 13 shows the extraction time profile for the 400° C. electrospun fiber-coated wire. The equilibration time for BTEX with the 400° C. fiber was approximately 30 minutes for benzene, toluene, ethylbenzene and o-xylene. FIG. 15 shows the extraction time profile for the 600° C. electrospun fiber-coated wire. The equilibration time for BTEX with the 600° C. fiber was approximately 60 minutes for benzene, and 30 minutes for toluene, ethylbenzene, and o-xylene. FIG. 16 shows the extraction time profile for the 800° C. electrospun fiber-coated wire. The equilibration time for the 800° C. fiber-coated wire was approximately, 30 minutes for benzene, toluene, ethylbenzene, and o-xylene.

Figure 11:
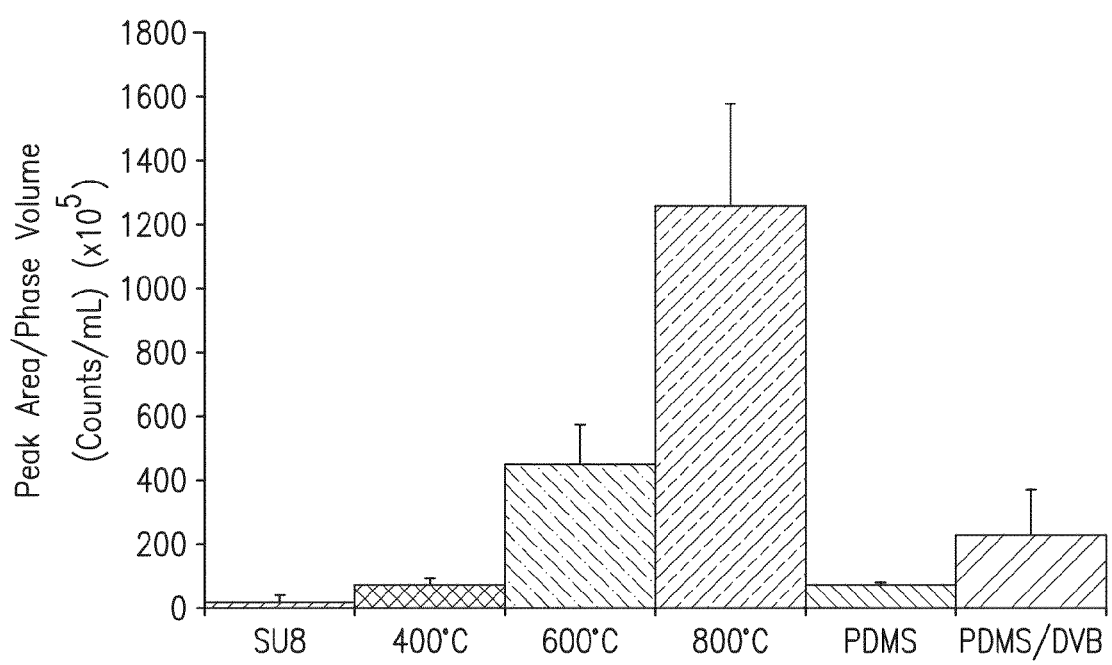
FIG. 11 is an extraction efficiency plot for benzene using various SPME systems.

The extraction performance of the electrospun fiber-coated wires was determined by comparing the fibers to the commercial fibers of PDMS and PDMS/DVB. FIG. 11 shows a bar graph comparing the extraction performance of each fiber for benzene. As shown in FIG. 16, the 800° C. electrospun fiber-coated wire was found to have higher extraction efficiency for benzene as compared to the other electrospun fiber-coated wires and the commercial fibers. It is remarkable that not only did the 800° C. have a higher extraction efficiency compared to the commercial fiber but the 600° C. fiber also had higher extraction efficiency.

The limit of detection and linear range for 600 and 800° C. electrospun fiber-coated SPME wires were examined for benzene and ethylbenzene. The detection limit of benzene determined for both fibers were 0.3 ng/ml (600° C.) and 0.4 ng/ml (800° C.) and for ethylbenzene was determined to be 0.9 ng/ml (600° C.) and 1 ng/ml (800° C.). It is interesting to point out that both of these fibers have a wide linear range (0.05-40 μg/ml) for a small coating thickness. The large linear range can be attributed to the high surface area of the nanofibers. The detection limits for both the 600 and 800° C. electrospun fiber-coated fibers are comparable to previously published SPME coatings but the linear range of these coated wires was larger than previously reported SPME fibers.

For extracting phenol, 4-chlorophenol, and 4-nitrophenol, the aqueous solution was acidified and saturated with NaCl as above. The extraction time profiles for the SU-8, 400° C., 600° C., and 800° C. electrospun fiber-coated wires were examined from 0 to 90 minutes for the above phenolic compounds. The extraction profile for the SU-8 electrospun fiber-coated SPME wire is shown in FIG. 16.

Figure 17:
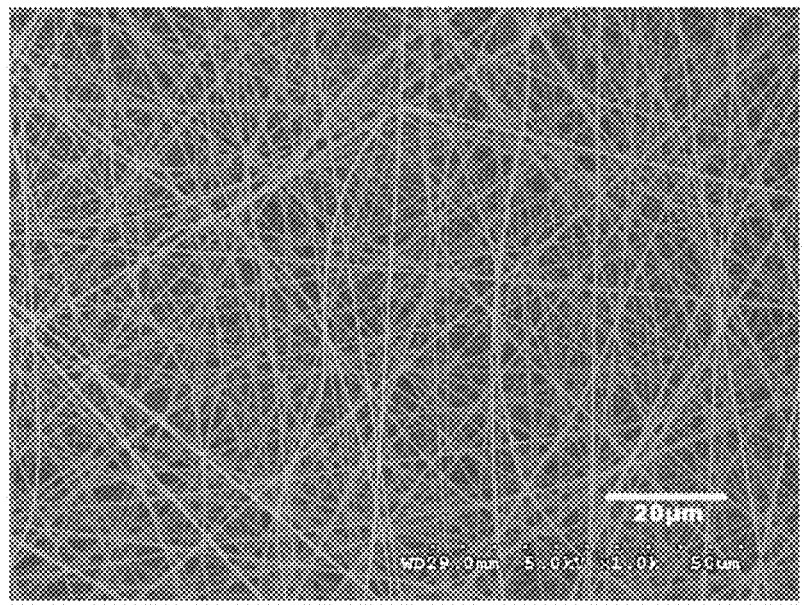
FIGS. 17 and 18 are a set of SEM images (FIG. 29 being at a higher magnification) of a plan view of an embodiment of a TLC plate manufactured under the electrospinning technique.
Figure 18:
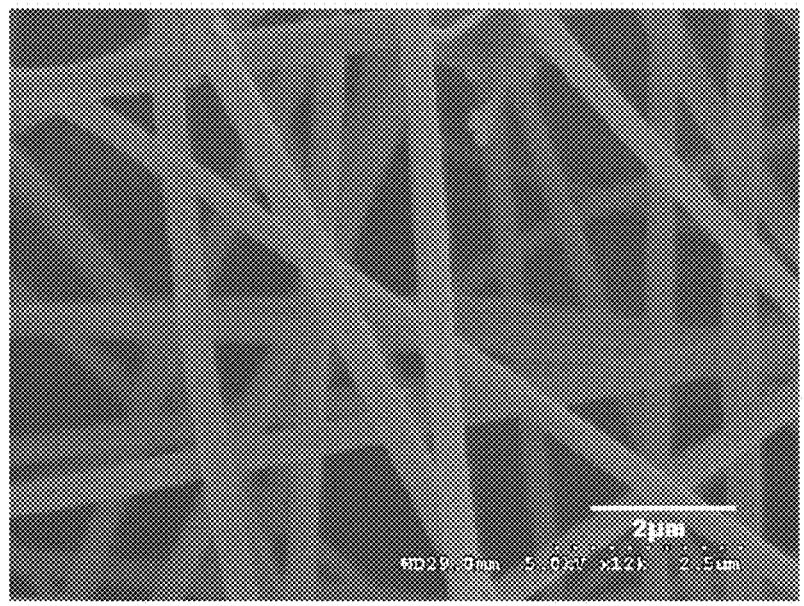
Figure 19:
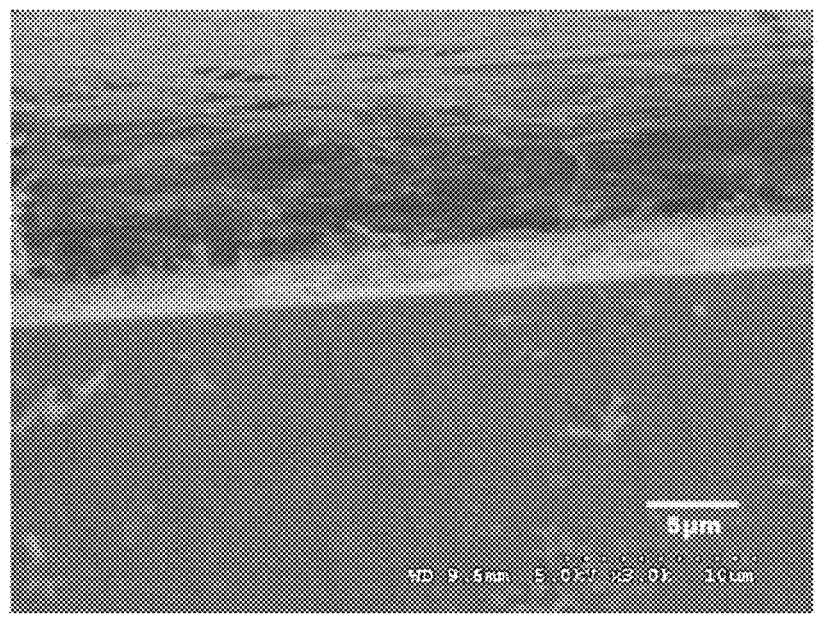
FIG. 19 is an SEM image of an edge-on electrospun TLC device.

For the pyrolysis temperatures of 400, 600, and 800° C., the extraction time profile for the phenolic compounds are shown below. The extraction time profile of the 400° C. is shown in FIG. 17. For the 600° C. electrospun-coated SPME fiber, the extraction time profile is shown in FIG. 18. The extraction time profile for the 800° C. SPME fiber is shown in FIG. 19. The wide range of effective pyrolysis temperatures demonstrate the high thermal stability of the electrospun fibers.

Figure 20:
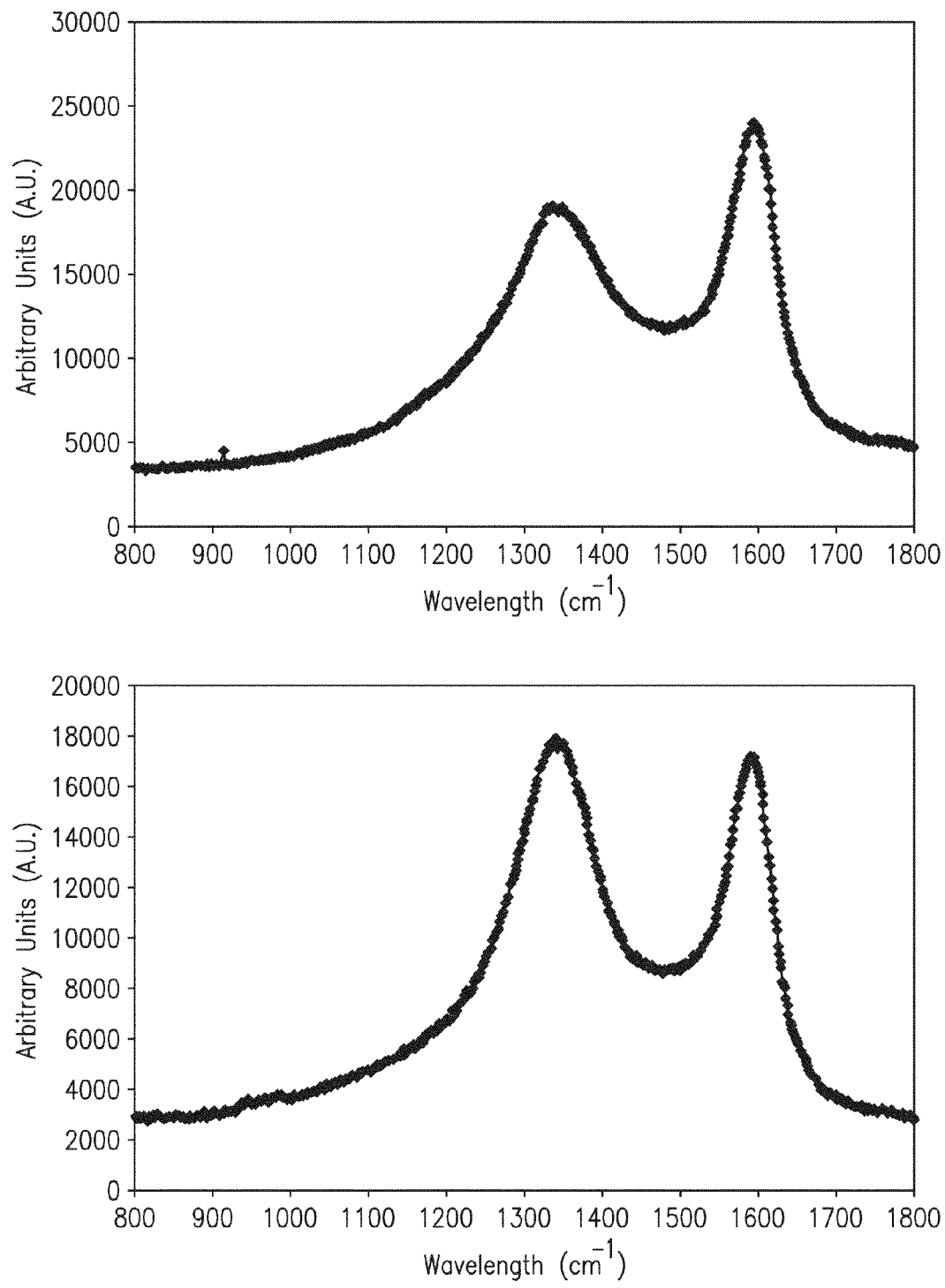
FIG. 20 shows characteristic Raman spectra of electrospun SU-8 samples pyrolyzed at 600° C. (A) and 1000° C. (B)

The extraction performance of the four electrospun wires compared to a commercially available polyacrylate (PA) SPME was examined for the three phenolic compounds. A representative result, that for 4-nitrophenol is shown in FIG. 20. Both the 600 and 800° C. electrospun-coated SPME fibers displayed higher extraction efficiencies than the PA fiber for phenol. For 4-chlorophenol, the 800° C. fiber demonstrated superior extraction performance as compared to the PA fiber; the extraction efficiency of the 600° C. was comparable to that of the PA fiber. The 600 and 800° C. electrospun coated-wires showed greater performance than the PA fiber for 4-nitrophenol; the efficiency of the SU-8 SPME fiber was comparable to that of the commercial fiber.

Since it displayed adequate extraction efficiency for all of the phenolic compounds, the SU-8 electrospun fiber-coated wire was chosen to be analyzed for limit of detection and linear range for phenol, 4-chlorophenol, and 4-nitrophenol. For the SU-8 fiber coated SPME wire, the limit of detection was determined to be 3 ng/mL for phenol, 2 ng/mL for 4-chlorophenol, and 7 ng/mL for 4-nitrophenol. The SU-8 fiber-coated wire also showed a large linear range for each of the compounds. It had a linear range of 0.004 μg/mL to 4 μg/mL for both phenol and 4-nitrophenol, while 4-chlorophenol had a linear range from 0.01 μg/mL to 10 μg/mL. This demonstrates the ability of the fiber to be used for a wide range of sample concentrations.

Electrospun Stationary Phase TLC

The electrospinning technique taught above also has industrial applicability in the field of thin layer chromatography (TLC). Electrospun fibers permit the thickness of the TLC stationary phase to be reduced from the typical 150 to 250 µm range to a range of about 3 to about 30 µm. The technique also allows a significant reduction in the diameter, from the micro to the nano scale, providing a method to tailor efficiency and speed of separation.

In a first embodiment of a TLC technique that the fibers facilitate, a TLC stationary phase was prepared by an electrospinning technique as described above, but where a polyacrylonitrile (PAN) was spun instead of SU8. The particular PAN selected had a molecular weight of about 150,000. Anhydrous dimethylformamide (DMF) was selected as the solvent for the PAN and the electrospinning solution was 10% (wt/vol) PAN in DMF. An aluminum foil was used as the collector substrate rather than a silicon plate. It was demonstrated that a plate can be produced in less than ten minutes with no sacrifice in quality or reproducibility.

It will be understood from the ability to provide appropriate fibers by electrospinning both a photo resist material and a highly polar polymer such as a polyacrylonitrile, that the technique taught herein may be applied to vary the nature of a TLC stationary phase to include a stationary phase with polar moieties, nonpolar interactions, hydrogen bonding interactions, adsorptive behavior, high porosities, etc. Further, the work has demonstrated that the electrospun fibers can be successfully pyrolyzed to provide carbon nanofibers for TLC stationary phase.

Materials that were selected for TLC using the PAN electrospun plate include the steroids cholesterol, androsterone and cortisone. For the testing, the mobile phases examined were a normal phase, consisting of mixtures of petroleum ether, with acetone, ranging from 0 to 100% acetone and a reversed phase, consisting of acetone and water mixtures ranging from 0 to 100% acetone.

Retardation factors for separation of the steroid analytes in the normal phase system using the electrospun PAN stationary phase are reported below. The results in the range of 30 to 50% acetone are not shown, as there was extreme horizontal broadening within that range. As a point of comparison, the same steroids were separated by the same normal phase mixtures in 10% acetone increments from 0 to 100% acetone.

Retardation factors for separation of the steroid analytes in the reversed phase system of water in acetone, using the electrospun PAN stationary phase are shown below. Unlike the normal phase experiment, the electrospun PAN plate was useful across the entire range of from 0 to 100% water, with experiments conducted at 10% increments of water in acetone. The same steroids were separated by the same reversed phase mixtures in 10% acetone increments from 0 to 100% acetone. In the reversed phase experiment, it is notable that cholesterol, the least polar compound, is the only one completely retained on the electrospun PAN plate at any point in the experiment, in contrast to the performance of the steroid analytes on the conventional TLC plate. It is further notable that cortisone, as the most polar analyte, is retained almost uniformly through the entire mobile phase range on the electrospun PAN plate, while the retardation factor for cortisone declines in a similar fashion to the other analytes on the conventional TLC plate.

| Compound | Distance | Solvent distance | Ave. Rf | Ave. w | Ave. k' | Ave. N |
|---|---|---|---|---|---|---|
| Cholesterol | 0 | 32 | 0 | 3.4 | 0 | 0 |
| Androsterone | 11.6 | 32 | 0.36 | 2.6 | 1.9 | 625 |
| Cortisone | 22.4 | 32 | 0.7 | 3.6 | 0.44 | 1000 |

A further experimental confirmation of the efficacy of the electrospun PAN TLC plate, compared to conventional TLC, was provided by selecting a set of 7 laser dyes from Exiton, Inc. as the test analytes. These analytes are all fluorescent in the visible range when excited by UV radiation. The seven selected dyes are Sulforhodamine 640, (S640) Pyromethene 597 (P597), Rhodamine 610 perchlorate (R610P), Rhodamine 610 chloride (R610C), Rhodamine 590 chloride (R590C), Rhodamine 101 (R101) and Kiton Red (KR). From the data obtained, the following table of retardation factors was calculated:

| Compound | Ave Rf Silica plate | Ave Rf E-spun plate | % RSD Rf Silica plate | % RSD Rf E-spun plate |
|---|---|---|---|---|
| S640 | 0.66 | 0.69 | 4.7 | 6.8 |
| P597 | 0.81 | 0.67 | 19 | 9.7 |
| R610P | 0.16 | 0.59 | 18 | 13 |
| R610C | 0.16 | 0.6 | 13 | 23 |
| R590C | 0.50 | 0.42 | 35 | 24 |
| R101 | 0.08 | 0.64 | 23 | 23 |
| KR | 0.63 | 0.67 | 5.5 | 15 |

For the same compounds, the experiments provide a comparison of efficiencies between a conventional silica plate and the electrospun embodiment:

| Compound | Ave N Silica plate | Ave N E-spun plate | % RSD N Silica plate | % RSD N E-spun plate |
|---|---|---|---|---|
| S640 | 9400 | 2000 | 79 | 58 |
| P597 | 1300 | 2400 | 42 | 110 |
| R610P | 51 | 390 | 57 | 86 |
| R610C | 85 | 970 | 66 | 110 |
| R590C | 18 | 120 | 59 | 190 |
| R101 | 29 | 970 | 64 | 99 |
| KR | 1400 | 1500 | 52 | 90 |

From the foregoing dye data, a few notable points are that the retardation factors and precisions obtained using the electrospun plates compare favorably to the conventional silica plates, that the electrospun plates exhibit higher efficiencies, although at a larger uncertainty level, and that complete separations are accomplished in 15 of 21 mixtures by the electrospun compared to 19 of 21 complete separations using the silica plate. The electrospun plate was able to completely separate S640 from KR, while a silica plate could not, and neither TLC plate could completely separate R610P from R610C.

Carbon Nanofiber Stationary Phase Thin Layer Chromatography

While still in widespread use today, TLC has drawbacks. Recent advances in TLC technology such as High Performance TLC (HPTLC) and Ultrathin TLC (UTLC) have helped to address some of these weaknesses. HPTLC allows for TLC stationary phases with smaller dimensions, allowing TLC to be used for quantitative as well as qualitative analysis. UTLC is a more recently developed method and has been found to further improve sensitivity and to reduce both analysis time and amount of consumable required for TLC.

Commercially available TLC plates are typically composed of a stationary phase with a thickness that ranges from 100-400 μm whereas UTLC plates created using monolithic silica gel or other sorbent materials have layers in the 5-30 μm range. The main drawback of UTLC is the low sample capacity. Many materials have been studied for use in TLC, including activated carbon which encountered issues with retention mechanisms of the analytes, the need for more exotic binders to adhere the new mixtures to the plates, and when coupled with silica gel, it was found that the percentage of activated carbon could not exceed 16%.

Like activated carbon, glassy carbon (also termed graphitized carbon) has potential as a sorbent for chemical separation. Moreover, like graphite, glassy carbon is a hydrophobic, yet highly polarizable solid. As such, glassy carbon can retain very polar analytes, such as cations and anions, which conventional C18 sorbents cannot, making glassy carbon especially desirable as a reversed phase sorbent for chromatography.

Conventional TLC systems, including those that employed activated carbon as a sorbent generally require binders or support materials to adhere the stationary phase to the plate. However, electrospinning polymers directly to the support plate and subsequent conversion of the polymer nanofibers into carbon nanofibers, reproducibly delivers a suitable medium for UTLC separation and analysis without binders.

Silicon wafers or stainless steel plates were cut into rectangular pieces; the substrate was placed on a ring stand and grounded. Each TLC plate was electrospun with SU-8 2100 solutions for either 15 or 20 minutes. After the electrospinning was finished, the plates were pyrolyzed using substantially the same methods discussed above.

The plates were then spotted with ~50 nL of the sample using a 250 μm internal diameter glass capillary and developed in 5 mL of mobile phase. The mobile phase was allowed to equilibrate with the vapor phase for 10 minutes prior to analysis. The mobile phase used for the laser dye studies was 2-propanol (Sigma-Aldrich, Atlanta, Ga.). 20 mM borate buffer formed in 90:10 water to acetonitrile was used as the mobile phase for amino acid analysis.

In order to overcome problems of carbon stationary phase (dark color) and visualize the analytes on the carbon stationary phase, a small amount of water or mobile phase was placed on top of the plate while it was placed horizontally and viewed under UV radiation.

The test analytes were six laser dyes acquired from Exciton Inc. (Dayton, Ohio) and were examined in two groups containing structurally similar compounds, Group A.: rhodamine 610 perchlorate (CAS: 23857-51-4), rhodamine 610 chloride (CAS: 81-88-9) and kiton red (CAS: 3520-42-1); and Group B.: sulforhodamine 640 (CAS: 60311-02-6), pyrromethene 597 (CAS: 137829-79-9), and rhodamine 101 (CAS: 72102-91-1). DL-phenylalanine, L-lysine and L-threonine were available commercially. An unmodified standard silica phase with particle sizes of 5-17 BET surface area of ~500 $m^2/g$, mean pore size of 60 Å, 0.75 mL/g pore volume, and layer thickness of 200 μm was used.

Fibers resulting from three different pyrolysis temperatures: 600, 800 and 1000° C., were examined. Fiber diameters and mat thicknesses for each pyrolysis temperature are shown in Table 1. The average fiber size of the glassy carbon fibers decreases with pyrolysis temperature which is consistent with typical observations of the evolution of low molecular weight compounds, condensation and shrinkage that occurs when converting polymers into carbon.

Raman spectroscopy was used to characterize the glassy carbon nanofiber stationary phase resulting from different pyrolysis temperatures. Characteristic Raman spectra of electrospun SU-8 samples pyrolyzed at 600° C. (A) and 1000° C. (B) are shown in FIG. 20. They show the classic D (~1350 $cm^{-1}$) and G (~1580-1600 $cm^{-1}$) bands associated with glassy carbon. There is an obvious shift in the ratio of the peak areas of the D and G peaks as the pyrolysis temperature increases In order to analyze the stationary phase thickness, a TLC device was fabricated and then the substrate was cleaved and placed on its side on an SEM stage in order to view the stationary phase in an "edge on" manner. A representative image is shown in FIG. 19.

Each plate was used for at least 35 trials before performance or physical structure diminished. After the plates were no longer usable, the carbon nanofiber stationary phase was simply removed by scrubbing the substrate and then cleaning with acetone.

Figure 21:
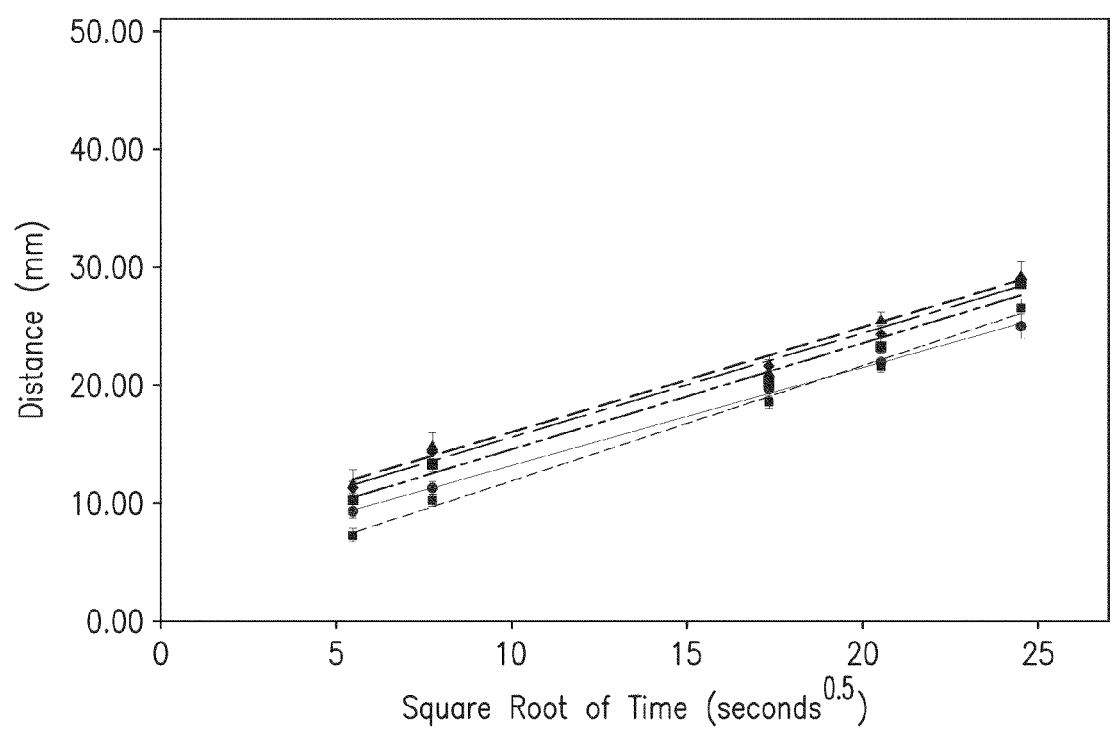
FIG. 21 shows the migration distance of the mobile phase versus the square root of the migration time.

One of the advantages of ultrathin-layer chromatography is the decrease in analysis time due to increased mobile phase velocity. FIG. 21 shows the migration distance of the mobile phase versus the square root of the migration time. This plot compares the relative mobile phase velocities in each of the carbon devices as well as the PAN UTLC device and a conventional silica gel plate.

When comparing the glassy carbon devices, it is clear that the largest observed fiber diameters demonstrate the fastest mobile phase velocities and this transport velocity decreases as a function of fiber diameter. The largest average fiber diameters are seen in the 600° C. device followed by the 800° C. and 1000° C. devices. The electrospun PAN UTLC device shows a mobile phase velocity very similar to the velocity observed for the 600° C. carbon device and the average fiber diameters for the two devices were of similar magnitude. The commercial silica gel TLC plate shows a mobile phase velocity similar to the 1000° C. carbon device.

Figure 22:
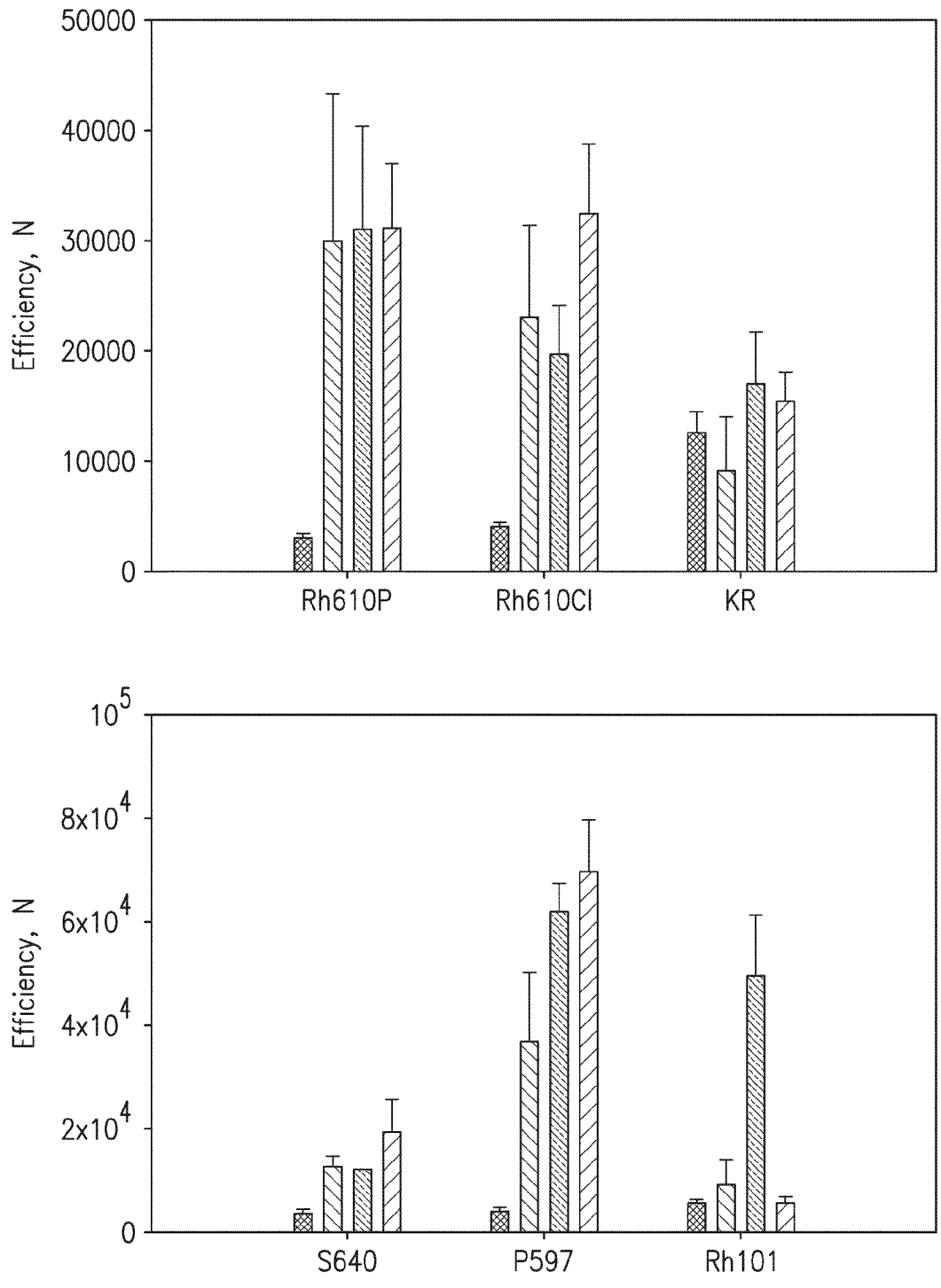
FIG. 22 shows a comparison of electrospun glassy carbon UTLC devices with electrospun PAN UTLC devices for the analysis of laser dyes.

In this study, electrospun glassy carbon UTLC devices are compared with electrospun PAN UTLC devices for the analysis of laser dyes in FIG. 22. The highest efficiency varied based on different analytes but was typically obtained using the 800 or 1000° C. carbon plate. It is noteworthy that for each dye, at least one of the electrospun glassy carbon UTLC devices demonstrates higher efficiency than the PAN UTLC device which was previously shown to be a highly efficient technique.

With the exception of one compound, rhodamine 101, the efficiency increased as a function of processing temperature. In all cases, the efficiency increased between the 600° C. plate and the 800° C. plate. All analyses using the electrospun glassy carbon stationary phase showed greater efficiency than the PAN UTLC phase which was also substantially higher than silica TLC devices commercially available.

Figure 23:
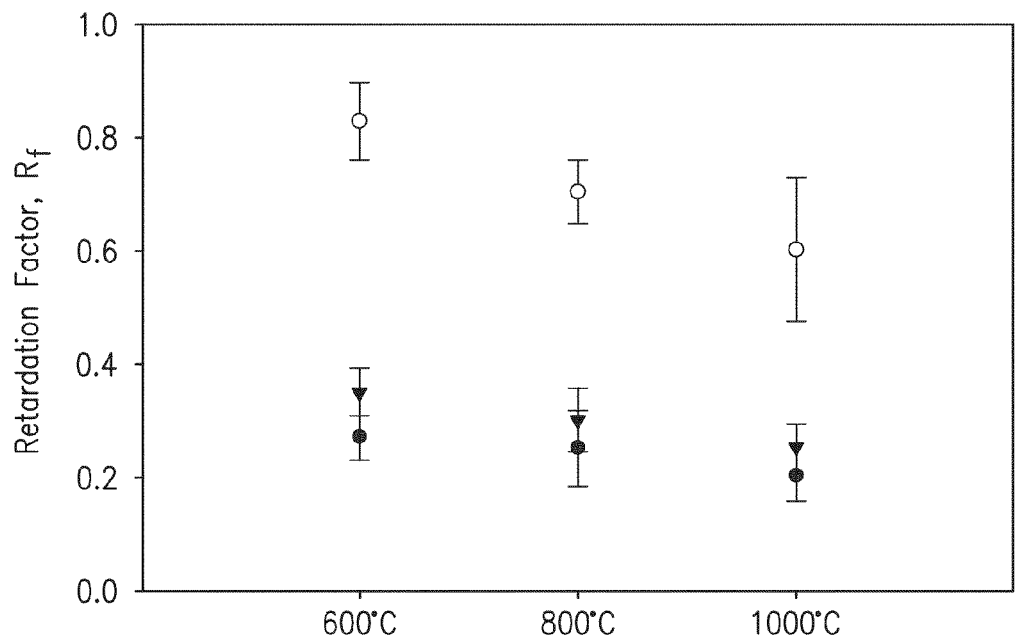
FIG. 23 shows retardation factors for replicate studies with, n=7, for each laser dye.

The retardation factors for replicate studies with, n=7, for each laser dye are shown in FIG. 23. The plots illustrate that the general trend for both groups of dyes is a decrease in the Rf value with increasing pyrolysis temperature. This means that the laser dyes are more strongly retained as the pyrolysis temperature increases. The decrease in retardation factor of the highly aromatic laser dye compounds is expected due to stronger π-π and dispersive interactions at higher processing temperatures. The data are supported by previous studies of glassy carbon that show polarizability becomes an important factor at higher temperatures.

The electrospun carbon UTLC technique showed a much higher resolution for all components of the laser dye mixture when compared to the electrospun PAN UTLC method.

Fluorescein isothionate (FITC) labeled amino acid solutions were prepared according to known procedures. The separations were carried out using a mobile phase composed of a 90:10 water to acetonitrile borate buffer solution with a pH of 9.5.

Figure 24:
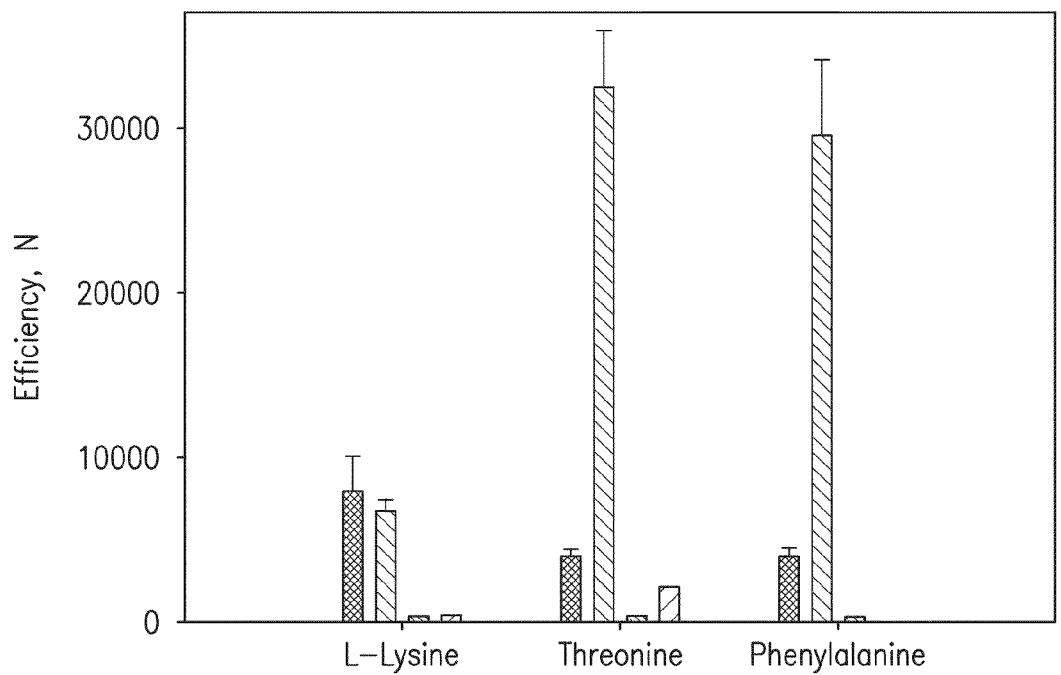
FIG. 24 presents the efficiency obtained using the glassy carbon UTLC devices in comparison to work by Khan et al.

FIG. 24 presents the efficiency obtained using the glassy carbon UTLC devices in comparison to work by Khan et al. The 600 and 800° C. carbon devices show a vast increase in efficiency when compared to the mixed cellulose phase. It is also worthy to note that highly efficient analysis were obtained using the glassy carbon UTLC technique using development times of 5 minutes and development distances of 3.5 cm while the comparison work used a development distance of 15 cm. The 1000° C. plate showed extreme band broadening and was clearly not optimal for essential amino acid analysis at these concentrations.

In order to examine the cause of the poor performance of the 1000° C. plates, the sample capacity of each of the electrospun glassy carbon UTLC devices was investigated. It was found that the 600 and 800° C. plates performed satisfactorily in the concentration range of $10^{-7}$ to $10^{-5}$ M while the 1000° C. device was overloaded at concentrations higher than $10^{-6}$ M.

Figure 25:
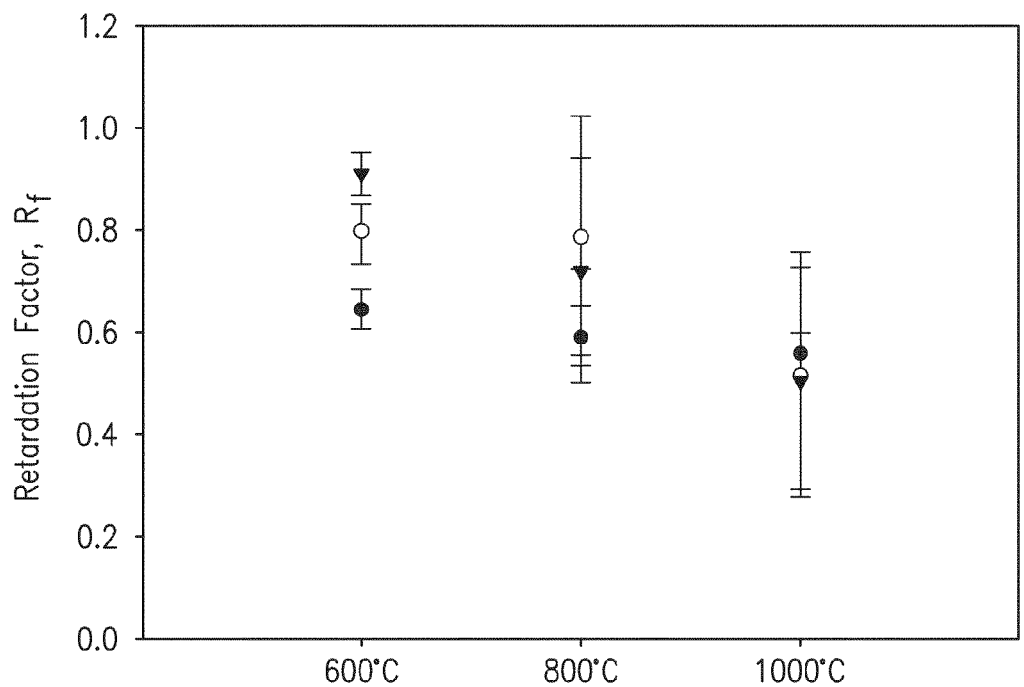
FIG. 25 shows the Rf values for each of the amino acids.

FIG. 25 shows the Rf values for each of the amino acids. The plot demonstrates the same trend as in the analysis of the laser dyes. The retardation factor of each amino acid decreases with increasing pyrolysis temperature. It is also interesting to note that the order of elution, Phe-Thr-Lys, changes to Thr-Phe-Lys between 600 and 800° C. This change in selectivity can be attributed to the increased $sp^2$-character of the stationary phase at 800 in comparison to the 600° C. plate. This is born out by the Raman spectra of these samples. These results illustrate the ability of the glassy carbon nanofibrous stationary phase to have tunable selectivity depending upon processing temperature.

Figure 26:
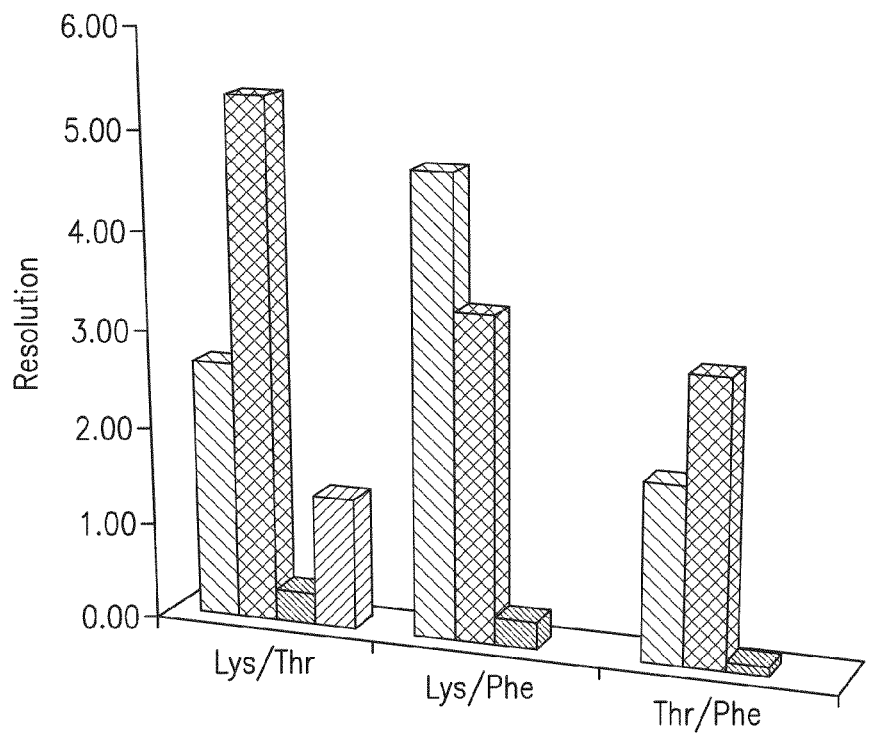
FIG. 26 demonstrates the separations obtained with the electrospun glassy carbon UTLC devices and comparison to previously published literature values.

FIG. 26 demonstrates the separations obtained with the electrospun glassy carbon UTLC devices and comparison to previously published literature values. The 800° C. devices showed the most desirable chromatographic performance for high efficiency separations of the ternary essential amino acid mixture. The electrospun carbon UTLC provides higher efficiency and resolution when compared to previous analyses. The results suggest that the mixture could be completely resolved at even shorter analysis times and development distances.

Additional Experimentation

Glassy carbon (GC) or porous graphitic carbon (PGC) are widely-used sorbents in chromatography. Due to its tunable retention behavior and both chemical and physical stability, glassy carbon has been used for HPLC, supercritical fluid chromatography (SFC), gas chromatography, as well as, solid phase extraction and microextraction (SPE and SPME). The most commonly-used type of glassy carbon is PGC, which is a very expensive sorbent that is fabricated by coating porous silica particles with a glassy carbon precursor, pyrolyzing the particles, then dissolving the silica particles leaving behind a porous glassy carbon material.

The glassy carbon nanofibers used herein have the same molecular structure as PGC, but are macroscopically non-porous. The electrospun glassy carbon nanofibers, like PGC, are amorphous and only demonstrate repeatable structure at nanoscopic levels. Glassy carbon surfaces are sheets of hexagonally oriented $sp^2$-hybridized carbon atoms. Nanoscopically, glassy carbon is composed of thin ribbons, with widths less than 10 nm. Like graphite, glassy carbon has two different types of carbon those located on the basal or edge-planes. Both carbons are $sp^2$-hybridized. The extent of delocalization of the $sp^2$-hybridization can be controlled by processing temperature, where higher temperatures yield enhanced delocalization.

Glassy carbon has not been used in thin-layer chromatography due in part to the detection problem that results from its dark color and ability to quench fluorescence. Past TLC work using activated carbon was performed by mixing with silica gel. This mixed phase was not ideal for TLC as the activated carbon to silica gel ratio strongly affected the retention mechanism and dispersion of the analytes. This study also showed that the maximum amount of carbon that could be incorporated into the stationary phase was 16%. So although activated carbon has previously been incorporated into a TLC method, to the best of our knowledge, this study is the first to employ a pure glassy carbon stationary phase for TLC. This work introduces a technique for the creation and use of an electrospun nanofibrous glassy carbon stationary phase that does not require support material or binders for use in reversed-phase ultra-thin layer chromatography.

The polymer used for the electrospinning experiments was SU-8 2100 negative photoresist (an epoxide polymer). SU-8 2100 was purchased from MicroChem Corp. (Newton, Mass.). The solvent used to prepare the dilute SU-8 2100 solutions was cyclopentanone (Sigma-Aldrich, Atlanta, Ga.). The test analytes were six laser dyes acquired from Exciton Inc. (Dayton, Ohio) and were examined in two groups containing structurally similar compounds; Group A: rhodamine 610 perchlorate (CAS: 23857-5194 4), rhodamine 610 chloride (CAS: 81-88-9) and kiton red (CAS: 3520-42-1); and Group B: sulforhodamine 640 (CAS: 60311-02-6), pyrromethene 597 (CAS: 137829-79-9), and rhodamine 101 (CAS: 72102-91-1). DL-phenylalanine from Eastman Chemical (Kingsport, Tenn.), L-lysine from Sigma-Aldrich and L-threonine from Calbiochem (Los Angeles, Calif.) were used. Electrospun polyacrylonitrile (PAN) UTLC plates were fabricated in house as described previously. Two commercially-available thin layer chromatography plates were purchased from Macherey-Nagel: a cyano functionalized silica (particle diameters of 2-10 μm, ~500 $m^2$/g BET surface area, 60 Å, 0.75 mL/g pore volume, and layer thickness of 200 μm on aluminum backing: (catalog number 818184) and an unmodified silica phase (catalog number 818133) with diameters of 5-17 μm and other physical attributes the same as the cyano modified phase.

Electrospinning is a simple and inexpensive method of producing nanofibers 108 composed of a polymeric material. All electrospinning experiments were conducted in a plexiglas enclosure which was used to control the temperature and humidity of the environment, as well as, serving to isolate the nanomaterials inside a closed system as a safety precaution. According to OSHA standards 1910.132 and 1910.134, air purifying respirators with cartridge filters having a sufficient assigned protection factor (APF) should be used when working with engineered nanomaterials when they are produced in the open lab. By maintaining the spinning process inside the plastic box no exposure is possible except when the process is completed and the box is opened. The electrospun fibers have one dimension which is not nano-sized. The fibers have diameters of ~400 nm, but they have macroscopic lengths that vary from the centimeter to meter range. Thus, a respirator is used purely as a precaution and the plastic enclosure is used to further reduce any potential risks. The optimized parameters for electrospinning SU-8 were previously examined in this group and found to be 75% (vol/vol) SU-8 in cyclopentanone, 0.02 mL/min flow rate, 9 kV, and 10 cm tip to collector distance. Because of the photo sensitive nature of SU-8 2100, all electrospinning experiments were performed in a dark room under yellow light. Due to differences in mass loss and shrinkage caused by varying processing temperatures, the electrospinning time was optimized for each device. In order to obtain a mat of fibers with a consistent thickness, devices pyrolyzed at 600° C. were spun for 15 minutes while devices processed to 800° C. and 1000° C. were electrospun for 20 minutes each. These conditions result in an electrospun glassy carbon nanofibrous mat with a thickness of ~15 μm after heat processing.

Figures 27A, 27B, 27C:
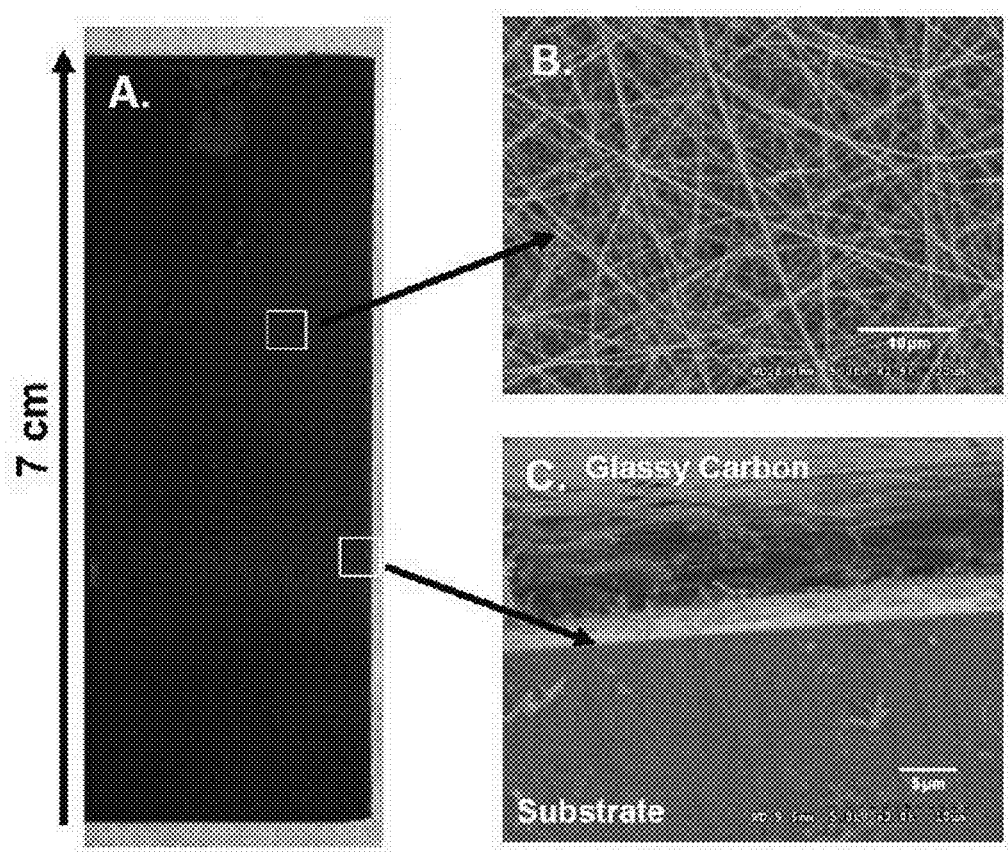
FIG. 27A is a digital photograph of an electrospun carbon UTLC device.
FIG. 27B is illustrations of an exemplary electrospun carbon UTLC device.
FIG. 27C is illustrations of an exemplary electrospun carbon UTLC device.

Stainless steel plates were cut into rectangular pieces approximately 2 cm×6 cm and cleaned with acetone prior to electrospinning. A plate was placed on a ring stand and grounded using an electrode from the high voltage power supply. After the electrospinning was finished, the SU-8 was crosslinked by exposing the fibers to ultraviolet light for 5 minutes. Previous work illustrates that electrospun SU-8 fibers do not retain their structure during pyrolysis unless this photo-polymerization step is taken. After the electrospun fibers were exposed to the UV radiation, they were placed directly into a tube furnace (Lindberg/Blue Waltham, Mass.) equipped with a PID (proportional, integral, derivative) temperature controller and heated to the specified pyrolysis temperature at a ramp rate of 2° C. per minute under a forming gas (N2/H2) environment. The plates were held at the pyrolysis temperature for at least 6 hours, then the oven was turned off and the samples were allowed to cool to room temperature. FIG. 27A-C illustrates the benchtop view of the electrospun glassy carbon UTLC plate.

The electrospun carbon UTLC plates were used without further treatment after the pyrolysis was complete. The plates were spotted with ~50 nL of the sample using a 250 μm internal diameter glass capillary and developed in 5 mL of mobile phase. The mobile phase was placed into a sealed cylindrical glass jar with an internal volume of 200 mL. The mobile phase depth in the development chamber was 3 mm. The chamber was sealed and allowed to equilibrate with the vapor phase for 10 minutes prior to analysis. This resulted in saturated conditions for the experiments. Mobile phase conditions were optimized for maximum resolution for both sample sets. The optimized mobile phase used for the laser dye studies was 2-propanol (Sigma-Aldrich, Atlanta, Ga.) while 20 mM borate buffer formed in 90:10 (volume:volume) water to acetonitrile was used for amino acid analysis. The development of a plate took approximately 5 minutes for each trial. After development, the plates were removed from contact with the mobile phase and dried at room temperature.

Figure 30:
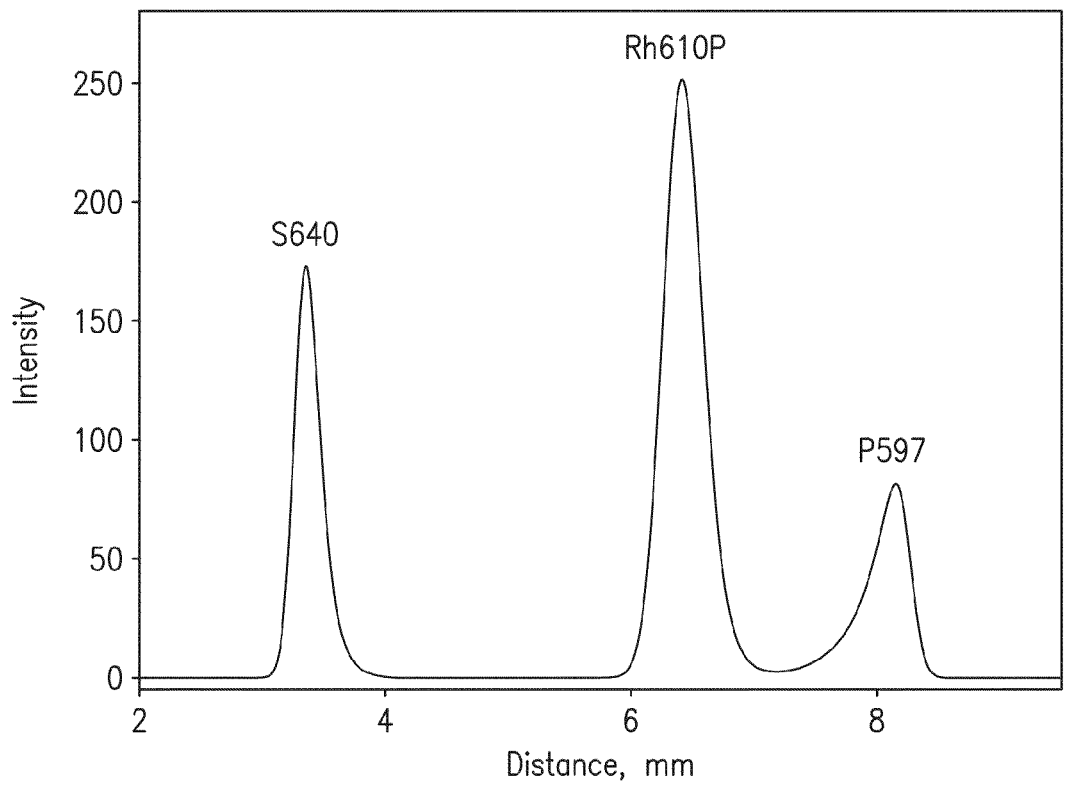
FIG. 30 is a chromotogram of the separation of a mixture of S640, Rh 610 P and KR on a 600° C. glassy carbon UTLC device with a developement distance of 1.5 cm.
Figure 32:
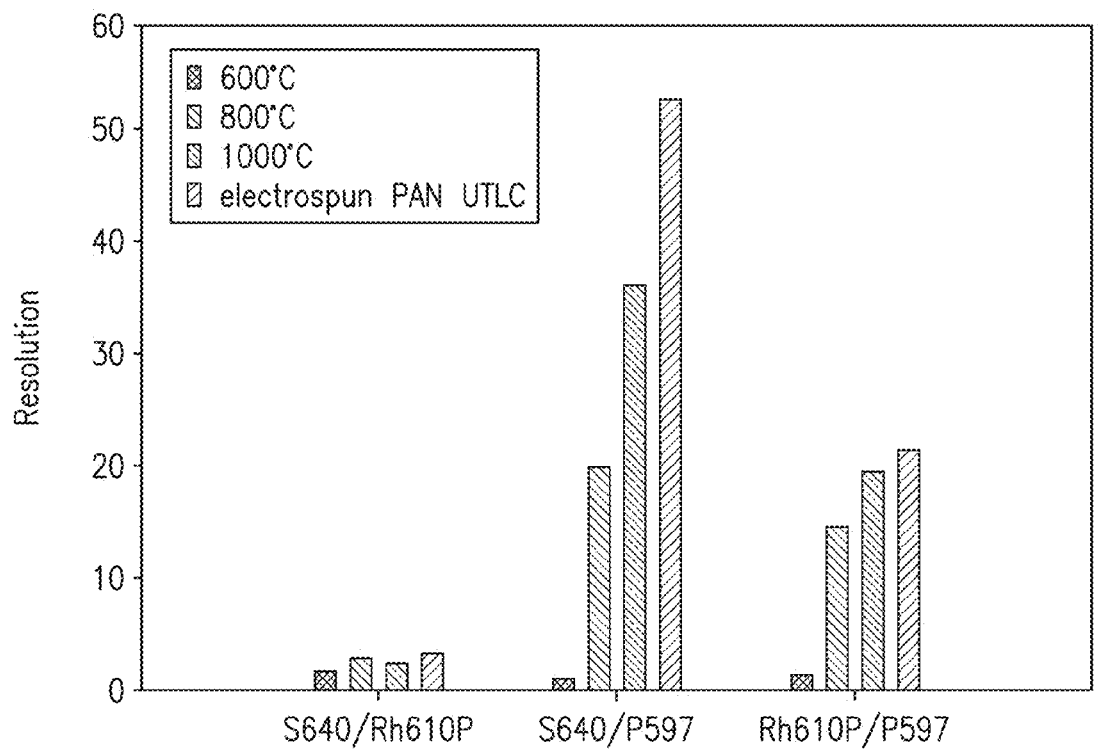
FIG. 32 is a graphical comparison of the resolution of a ternary mixture of laser dyes using various UTLC devices.

A digital documentation system obtained from Spectroline was used for all UTLC visualization: CC-81 cabinet with ENF-280C 365 nm/254 nm, 8 Watt UV Lamp; GL-1301 universal camera adapter with 58 mm adapter ring along with a Canon A6501S12.1 MP digital camera to collect the images. Data was obtained by obtaining a photograph of each separation using a digital photograph, analyzing the image and obtaining raw data using TLC Analyzer, then using Peak-Fit to analyze the chromatographic parameters of the separation. Analyses of digital images were performed using TLC Analyzer software available at: http://www.sciencebuddies.org/science-research-papers/tlc_analyzer.shtml. A digital image is made up of many rows and columns of pixels. Thus, a digital image is essentially a matrix of numbers, and TLC Analyzer analyzes images by panning across the matrix and combining moving averages to create a chromatogram. Representative digital photographs and/or the resulting chromatograms are shown in FIGS. 30 and 32.

The lack of commercially-available electrospun and/or carbon TLC devices present a challenge for comparison of our results. In a recent comprehensive review, only two methods for preparing UTLC devices are reported, and neither one is commercially-available. As a result of this, the electrospun carbon UTLC devices were compared to polymer UTLC devices using electrospun fibers, as well as, the two commercially-available, silica based sorbents from Macherey-Nagel.

All nanoscopic images of the electrospun fibers were obtained using a Hitachi S-4300 (Hitachi High Technologies, America, Inc., Pleasanton, Calif., USA) scanning electron microscope (SEM). The electrospun SU-8 fibers were pyrolyzed using a Lindberg Blue (Waltham, Mass.) tube furnace. A Sunray 400SM UV flood light (Uvitron International West Springfield, Mass.) was used to crosslink the SU-8 fibers before pyrolysis. Raman spectra were obtained using a Renishaw InVia Raman Microscope (Gloucestershire, UK) with Argon laser excitation at 514.5 nm.

Electrospun carbon UTLC plates processed to three different pyrolysis temperatures: 600, 800 and 1000° C., were examined. A representative SEM image of the fibers is shown in FIG. 1B. Fiber diameters and mat thicknesses for each pyrolysis temperature are shown in Table 1.

TABLE 1

Description of the all devices used for TLC studies.

| Device | Mat Thickness (μm) | Avg. Fiber Diameter |
|---|---|---|
| 600° C. | 16 ± 1.4 | 330 ± 70 nm |
| 800° C. | 14 ± 1.0 | 300 ± 70 nm |
| 1000° C. | 13 ± 1.5 | 220 ± 70 nm |
| PAN UTLC | 24 ± 1.8 | 395 ± 55 nm |
| Silica Gel | 200 | 2-10 μm* |

(*Particle Diameter)

The average diameter of the glassy carbon fibers decreases with pyrolysis temperature which is consistent with typical observations of the evolution of low molecular weight compounds, condensation and shrinkage that occurs as the carbon is further graphitized.

In order to analyze the stationary phase mat thickness, a TLC device was fabricated and then the substrate was cleaved and placed on its side on an SEM stage in order to view the stationary phase in an "side-view" manner. A representative image is shown in FIG. 27C.

To confirm the glassy carbon structure of the SU-8 nanofibers after pyrolysis, Raman spectroscopy was performed. A detailed description of the analyses and the resulting spectra can be found in the Supplemental Information section. The findings were consistent with other reports of glassy carbon-like materials. From the Raman spectra, the average microcrystallite size, $L\alpha$, (shown in Table 2) of the glassy carbon was calculated using the Tuinstra and Koenig equation and was found to decrease with increasing processing temperature. $L\alpha$ was determined to be between 1 and 3 nm for each of the electrospun glassy carbon UTLC plates, which is typical of glassy carbon at processing temperatures between 600° C. and 1000° C.

TABLE 2

Comparison of effective pore radii, microcrystallite size, and κ values for each of the TLC devices examined.

| TLC Device | Effective Pore Radius, R | $L_\alpha$ | κ (cm2/sec) |
|---|---|---|---|
| Silica Gel | 345 ± 20 nm | N.A. | 0.019 |
| PAN UTLC | 515 ± 10 nm | N.A. | 0.028 |
| 600° C. | 475 ± 35 nm | 2.99 nm | 0.026 |

TABLE 2-continued

Comparison of effective pore radii, microcrystallite size, and κ values for each of the TLC devices examined.

| TLC Device | Effective Pore Radius, R | $L_a$ | κ (cm2/sec) |
|---|---|---|---|
| 800° C. | 400 ± 15 nm | 2.39 nm | 0.022 |
| 1000° C. | 380 ± 25 nm | 1.47 nm | 0.020 |

Heptane was the mobile phase for the calculation of R. N.A.—not applicable.

When glassy carbon is heated, the $sp^2$-hybridization of the carbon lattice increases which causes enhanced delocalization of the π electron cloud. Accordingly, enhanced π-π interactions with analytes also occurs with increased processing temperature. The fabrication of electrospun glassy carbon UTLC plates in this manner allows for the UTLC devices to have tunable retention dependent upon processing temperature.

The electrospun carbon UTLC devices proved to be chemically and mechanically robust over a large number of experiments. Each plate was used for at least 35 trials before performance or physical structure diminished. After the plates were no longer usable, the carbon nanofiber stationary phase was simply removed by scrubbing the substrate and then cleaned with acetone. A new device for UTLC could then be created by electrospinning onto the reusable substrate.

The Lucas-Washburn equation (equation 1) is used to describe the capillary flow through porous media:

$$Z_f^2 = \frac{\gamma R t \cos\theta}{2\eta} \quad (1)$$

In this equation, Zf is the distance travelled by the solvent front, t is the corresponding time, γ and η are the surface tension and viscosity of the mobile phase, θ is the contact angle of the mobile phase with the stationary phase, and R is the effective pore radius.

Figure 28:
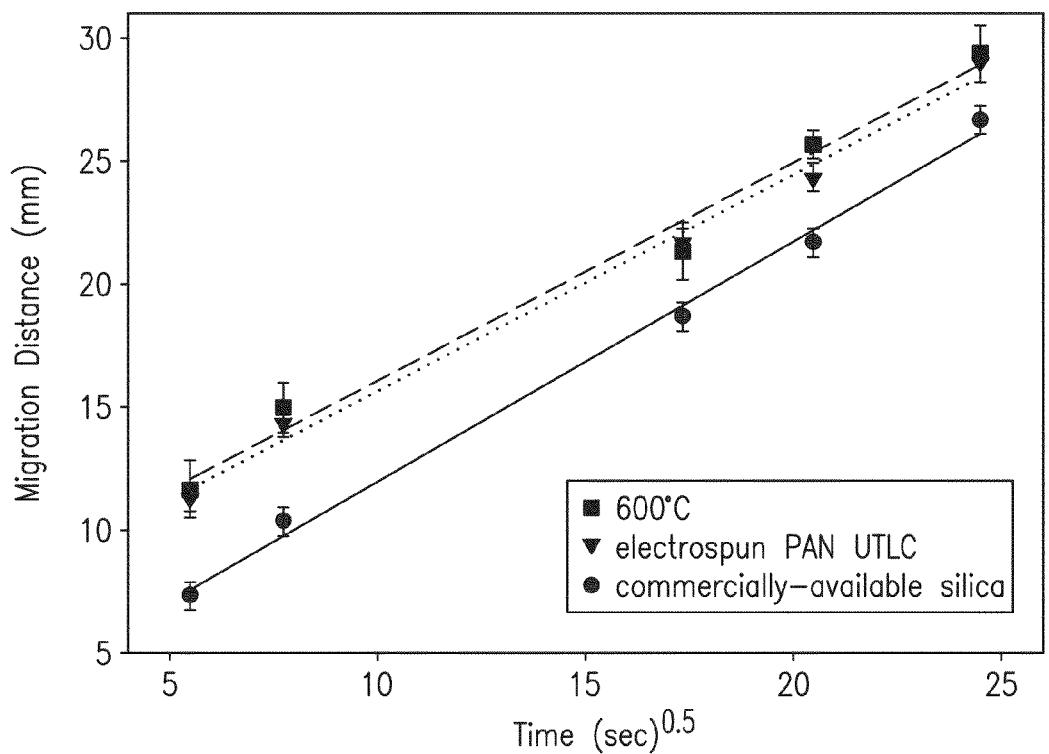
FIG. 28 is graphical comparison of mobile phase velocities.
Figure 29:
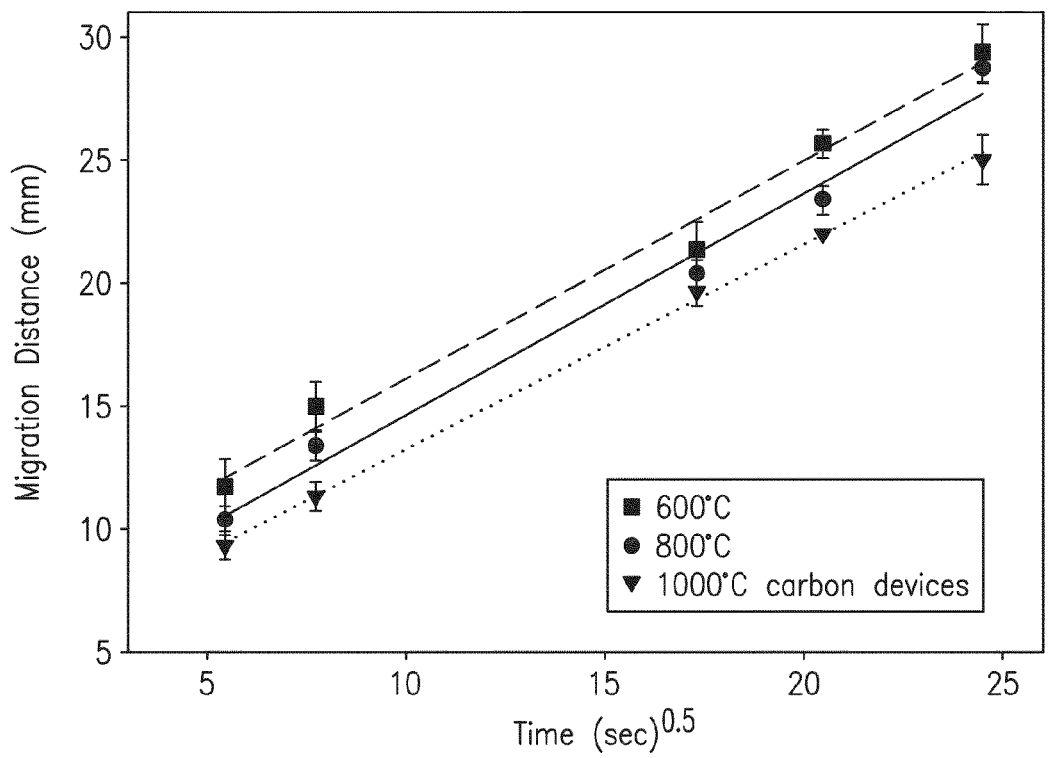
FIG. 29 is a graphical comparison of various carbon devices.

In order for the Lucas-Washburn equation to accurately describe a system, the following must be true: laminar flow conditions must prevail (Reynolds number<1200); an adsorbed film of penetrating liquid must exist (i.e. must expose to vapors of solvent and reach equilibrium before use); inertial influences must be negligible, and the contact angle of mobile phase on the surface must be 0. Equilibrium conditions apply in this study and thus all of these conditions are satisfied, as they are in most TLC experiments. To examine our system, plots of $Zf^2$ versus t are shown in FIGS. 28 and 29. FIG. 28 is a comparison of a 600° C. glassy carbon UTLC device with an electrospun PAN UTLC device as well as a commercially-available silica TLC plate. FIG. 29 compares the 600° C., 800° C. and 1000° C. electrospun glassy carbon UTLC devices. The linear fits show agreement with the Lucas-Washburn equation ($r^2$>0.98 for each).

When comparing the mobile phase migration using electrospun glassy carbon UTLC devices, FIG. 29, it is clear that the largest observed fiber diameters demonstrate the fastest mobile phase velocities and the transport velocity decreases as a function of fiber diameter (600° C.>800° C.>1000° C.). For example, the 600° C. device migrates ~15% farther than the 1000° C. device for the same development time. The electrospun PAN UTLC devices show a mobile phase velocity very similar to the velocity observed for the 600° C. carbon device and the average fiber diameters for the two devices were of similar magnitude. The commercial silica gel TLC plate shows a mobile phase velocity similar to the 1000° C. carbon device.

Kalogianni and co-workers previously used the Lucas-Washburn equation to measure the effective pore radii of porous media using nonpolar solvents which had 0° contact angles with the measured surfaces. Each mobile phase used for separations, as well as heptanes, showed 0° contact angles on the glassy carbon surfaces. Therefore, heptanes were used as the mobile phase to calculate effective pore radii for the three carbon devices, the electrospun PAN UTLC device, and a commercially available silica gel TLC plate. Using the Lucas-Washburn equation the effective pore radii, R were calculated (Table 2). Interestingly, the estimated effective pore radii, R, for the glassy carbon devices were approximately two to three times larger than the observed fiber radii that were measured using SEM while the calculated R for the commercially-available silica phase is ~⅓ of the particle diameter. The pore structures for the nanofibers and the commercially-available phases are clearly very different.

The velocity constant, κ, is often used to describe mobile phase transport in TLC. κ is a constant that replaces the term γR/2η in the Lucas-Washburn equation and also takes into account the average particle diameter, pore size distribution and permeability of the layer for typical precoated TLC layers. The velocity constant values were determined for each of the electrospun glassy carbon UTLC devices, an electrospun PAN UTLC device and a commercially-available silica gel TLC plate. As can be seen in Table 2, the values experimentally obtained for each of the commercially available TLC devices are similar to those previously reported for silica TLC plates using similar organic solvents and are on the order of $10^{-2}$ cm²/sec. However, all of the electrospun UTLC devices (PAN, as well as each glassy carbon device) demonstrate larger κ values than the commercially available silica gel plate meaning that faster mobile transport occurs in the electrospun UTLC devices. When a direct comparison of migration distance versus time is made, the 600° C. device is found to take approximately half of the time (3.6 min for electrospun UTLC) required to reach a development distance of 3.5 cm when compared to commercially-available silica plates (7 min).

The procedure for applying samples to each TLC plate is described above in section 2.4. The average starting spot width for the electrospun glassy carbon UTLC devices were 0.25-0.5 mm for the laser dyes and 0.5 mm for amino acids. Using the same sample application process on the silica leads to starting spot widths of 1 mm and 0.5 mm for the laser dyes and amino acids, respectively. Typically, resulting spot widths on the glassy carbon UTLC devices at the end of the development was 0.5 to 1 mm, with the largest average spot size being lysine at 2.85 mm on the 800° C. UTLC device. Therefore, the developed spot widths on the glassy carbon plate are similar to the initial sample spot widths.

Carbon is a fluorescence quencher. In order to overcome this problem and to visualize the analytes on the carbon stationary phase, a small amount of water or acetone was sprayed on top of the plate using a TLC reagent nebulizer (Kimble-Chase Vineland, N.J.) while the plate was horizontal and viewed under UV radiation. Addition of liquid to the dry plate causes desorption of the analytes from the glassy carbon stationary phase and their fluorescence can be observed. In order to check the validity of this visualization process, digital images were captured at 2 second intervals after the introduction of the liquid to the plate. A laser dye, sulforhodamine 640, was spotted on an electrospun carbon UTLC plate and then acetone was sprayed on the plate as digital images were captured every two seconds. The images were then analyzed using TLC Analyzer software and were found to have similar spot sizes (i.e. less than 5% increase in spot size) for up to 10 seconds after the visualization liquid was sprayed onto the plate, this was ample time for the digital camera to capture the analyte spots prior to loss of spot structure.

Laser dyes from Exciton Inc. were used as test analytes for the carbon TLC. Analysis of laser dyes is a common practice in development of new TLC techniques. The dyes were an ideal test set for the electrospun glassy carbon UTLC technique due to their ability to fluoresce with UV excitation, their high quantum yields, and their highly aromatic character. The dyes were initially examined individually as a proof of concept to demonstrate that analyte migration and differential retention were possible on the electrospun glassy carbon UTLC devices. Plate number, N, and retardation factor data presented here describes these experiments.

The retardation factor was calculated using equation 2 where ZS is the distance 318 travelled by the analyte spot and ZF is the distance travelled by the solvent front:

$$R_f = \frac{Z_S}{Z_F} \quad (2)$$

The retardation factors and standard deviation for replicate studies with, n=7, for each laser dye are shown in Table 3.

TABLE 3

Retardation factors ($R_f$) of laser dyes on each of the electrospun carbon UTLC devices.

| TLC Device | Rf | | | | | |
|---|---|---|---|---|---|---|
| | Rh 610 P | Rh 610 Cl | KR | S 640 | P 597 | Rh 101 |
| 600° C. | 0.56 ± 0.04 | 0.65 ± 0.10 | 0.44 ± 0.04 | 0.27 ± 0.04 | 0.83 ± 0.07 | 0.35 ± 0.04 |
| 800° C. | 0.32 ± 0.03 | 0.33 ± 0.03 | 0.29 ± 0.04 | 0.25 ± 0.07 | 0.70 ± 0.30 | 0.30 ± 0.05 |
| 1000° C. | 0.38 ± 0.05 | 0.28 ± 0.05 | 0.37 ± 0.03 | 0.20 ± 0.05 | 0.60 ± 0.25 | 0.25 ± 0.04 |

The data illustrate that the general trend for both groups of dyes is a decrease in the Rf value with increasing pyrolysis temperature. This means that the laser dyes are more strongly retained as the pyrolysis temperature increases. For example, the retention of rhodamine 610 chloride increases by ~50% between processing temperatures of 600 and 800° C. The decrease in retardation factor (increase in retention) of the highly aromatic laser dye compounds is expected due to stronger π-π interactions that occur with increased processing temperature. Not surprisingly the least retained (Rf=0.83) compound is pyrromethene 597 which is composed of a three ring system compared to all other compounds which have at least four. The most strongly retained compounds are sulforhodamine 640 and rhodamine 101 which are structurally similar. These two compounds are composed of 8 six-figured rings and thus interact strongly with the glassy carbon stationary phase via π-π and dispersive interactions.

In TLC, plate number, N, is directly proportional to the square of the ratio of analyte (solute) migration distance, ZS, to spot width, w.

$$N = 16\left(\frac{Z_S}{w}\right)^2 \quad (3)$$

Typically, conventional silica gel TLC and HPTLC devices developed using capillary flow have N ~250-5000. Poole predicted that plate numbers approaching 100,000 are possible using forced-flow HPTLC with 3 μm diameter particles and development times of 25 minutes. However, this would also require large pressure drops across the device. Electrospun UTLC is now providing high efficiency without the need of forced-flow HPTLC.

A previous direct comparison of commercially-available silica plates and electrospun polyacrylonitrile (PAN) UTLC plates with similar stationary phase chemical surface structure showed a vast improvement (1-3 orders of magnitude improvement in half the analysis time) in the efficiency of analysis of laser dyes and steroidal compounds. This increase in plate number was due in large part to the decrease in spot width (typically a factor of 5) demonstrated using the technique. The electrospun glassy carbon UTLC devices in this study show an even greater decrease in dispersion and therefore, spot width. A digital photograph of the separation of sulforhodamine 640, rhodamine 610 perchlorate and pyrromethene 597 was analyzed and the resulting chromatogram is shown in FIG. 30.

Figure 31:
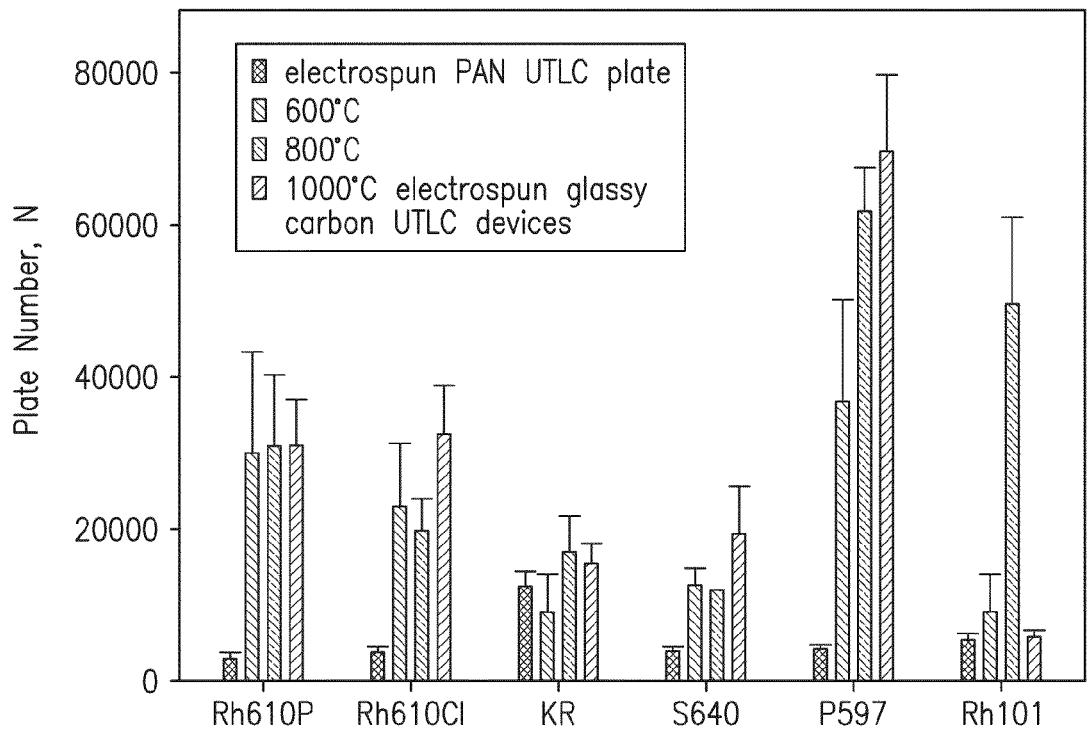
FIG. 31 is a graphical comparison of the plate number, N, obtained for the analysis of laser dyes on eletrospun PAN UTLC plate electrospun glassy carbon UTLC devices.

The plate numbers of electrospun glassy carbon UTLC devices processed at 600, 800 and 1000° C. are compared with those of electrospun PAN UTLC devices for the analysis of laser dyes in FIG. 31. For a given analyte, the processing temperature that gave the highest efficiency varied but was always obtained using either 800 or 1000° C. processed electrospun glassy carbon plates.

The resolution of a mixture of sulforhodamine 640, rhodamine 610 perchlorate, and pyrromethene 597 on the carbon devices and the electrospun PAN UTLC device, is shown in FIG. 31. The mixture was fully separated on each of the three carbon TLC plates. There is an increase in resolution as the processing temperature increases due to increased selectivity and higher efficiency separations. The electrospun carbon UTLC technique proved to be a much higher resolution method for all components of the laser dye mixture when compared to commercially-available TLC plates. To summarize, the electrospun glassy carbon UTLC plates show minimal band broadening, resulting efficiencies in the range of 10,000 and also prove to be a very high resolution technique for the analysis of laser dyes.

Figure 33:
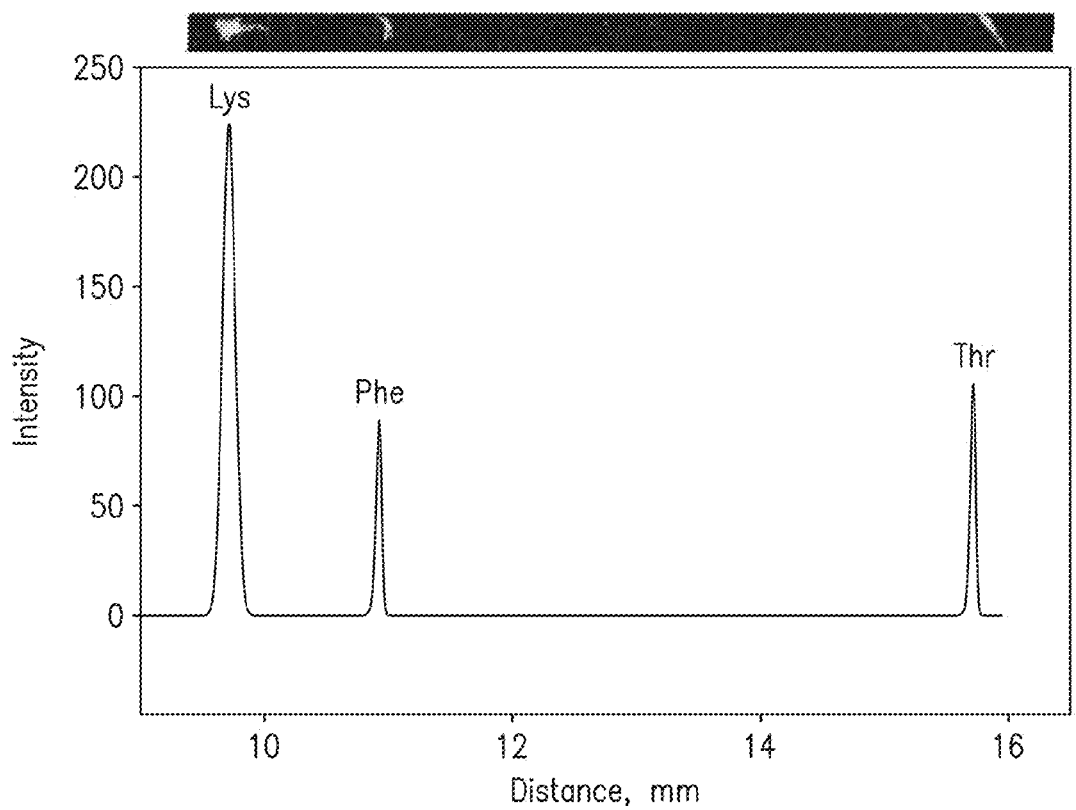
FIG. 33 is digital image and chromatogram of the separation of a mixture of lysine, threonine and phenylalanine on a 600° C. glassy carbon UTLC plate with a developement distance of 2.0 cm.

In order to study essential amino acids on the electrospun glassy carbon UTLC devices, lysine, threonine, and phenylalanine were labeled with fluorescein isothionate (FITC), using a previously reported method. FITC is commonly-used to fluorescently tag biomolecules such as amino acids and proteins. Separations were carried out using an optimized mobile phase composed of a 90:10 (volume:volume) water to acetonitrile borate buffer solution with a pH of 9.5. FIG. 33 is a chromatogram of the separation of lysine, threonine and phenylalanine on a 600° C. electrospun glassy carbon UTLC device.

Table 4 shows the Rf values for each of the amino acids.

TABLE 4

Retardation factors ($R_f$) of amino acids on each of the electrospun carbon UTLC devices.

| TLC Device | $R_f$ | | |
|---|---|---|---|
| | Lys | Thr | Phe |
| 600° C. | 0.64 ± 0.04 | 0.91 ± 0.04 | 0.79 ± 0.06 |
| 800° C. | 0.59 ± 0.06 | 0.72 ± 0.22 | 0.79 ± 0.23 |
| 1000° C. | 0.56 ± 0.04 | 0.50 ± 0.22 | 0.51 ± 0.24 |

The data demonstrate the same trend is as in the analysis of laser dyes. The retardation factor of each amino acid decreases with increasing pyrolysis temperature. Not surprisingly, lysine is the most strongly retained of the sample set. Under the separation conditions, lysine is the only analyte with a residual charge. Glassy carbon is known to be a highly polarizable material and the electrostatic charge of lysine under these conditions lead to strong retention of this compound. It is also interesting to note that the order of migration (least to most retained), Lys-Phe-Thr, changes to Lys-Thr-Phe between 600 and 800° C. This change in selectivity can be attributed to the increased $sp^2$-character and polarizability of the stationary phase processed to 800° C. in comparison to the 600° C. plate. Threonine, which contains a hydroxyl substituent, becomes more strongly retained at 800° C. These results illustrate the ability of the glassy carbon nanofibrous stationary phase to have tunable selectivity depending upon processing temperature.

Table 5 presents the plate numbers obtained using the glassy carbon UTLC devices in comparison to previously published data.

TABLE 5

Plate numbers obtained for analysis of amino acids using each electrospun glassy carbon UTLC plate and comparison to a mixed stannic arsenate/cellulose phase.

| | Plate Number, N | | | |
|---|---|---|---|---|
| Compound | 600° C. | 800° C. | 1000° C. | Cellulose[7] |
| Lysine | 37500 ± 4500 | 6800 ± 650 | 330 ± 40 | 370 |
| Threonine | 195000 ± 6100 | 32400 ± 3400 | 330 ± 20 | 2100 |
| Phenylaline | 476000 ± 7900 | 29600 ± 4500 | 290 ± 30 | N.A. |

The 600 and 800° C. carbon devices show a vast increase in efficiency when compared to results using the mixed cellulose phase described in. The 600° C. devices result in plate numbers in excess of 100,000 for threonine and phenylalanine over a development distance of 2.0 cm. As was the case with the test analytes, minimal band broadening occurred and typical developed spot widths were 2.5 mm or under for the 600° C. and 800° C. electrospun carbon UTLC devices. It is also worthy to note that highly efficient analyses were obtained using the glassy carbon UTLC technique using development times of 5 minutes and development distances of 3.5 cm or less while the comparison work used a development distance of 15 cm. The electrospun glassy carbon UTLC devices described in this study take a step towards one of the overall goals of UTLC which is to improve performance while reducing analysis time.

The 1000° C. plate showed extreme band broadening and was clearly not optimal for the essential amino acid analysis. In order to examine the cause of the poor performance of the 1000° C. plates, the sample capacity of each of the electrospun glassy carbon UTLC devices was investigated. It was found that the 600 and 800° C. plates performed satisfactorily in the concentration range of $10^{-7}$ to $10^{-5}$ M while the 1000° C. device was overloaded at concentrations higher than $10^{-6}$ M.

Previous work by both Poole and Guiochon demonstrated that in capillary flow, small particle (<10 μm) TLC and HPTLC, the plate height, H, increases as a function of development distance. For HPTLC using a support of 5 μm diameter silica particles, plate height was found to increase from ~50 to 130 μm between development distances of 4 and 10 cm. For all analytes studied using electrospun glassy carbon UTLC devices, the plate height either decreases or remains constant over the range of development distances (1-6 cm). The most strongly retained (lowest Rf value) amino acid, lysine, was found to have the most significant decrease in plate height (from 20 μm 418 to 10 μm) over the development range studied. Threonine and phenylalanine, which have similar Rf values, both showed similar behavior as plate height decreased from 3 to 1 μm over a development distance range of 4-6 cm. To the best of our knowledge, the only other report describing a decrease in plate height with increased migration distance uses pressurized planar electrochromatography (PPEC). This study reports a decrease in H from ~600 μm to 100 μm at migration distances of 5 and 70 mm, respectively. More detailed studies are currently being performed to elucidate the mechanism of the enhanced performance seen in the electrospun glassy carbon UTLC devices.

Figure 34:
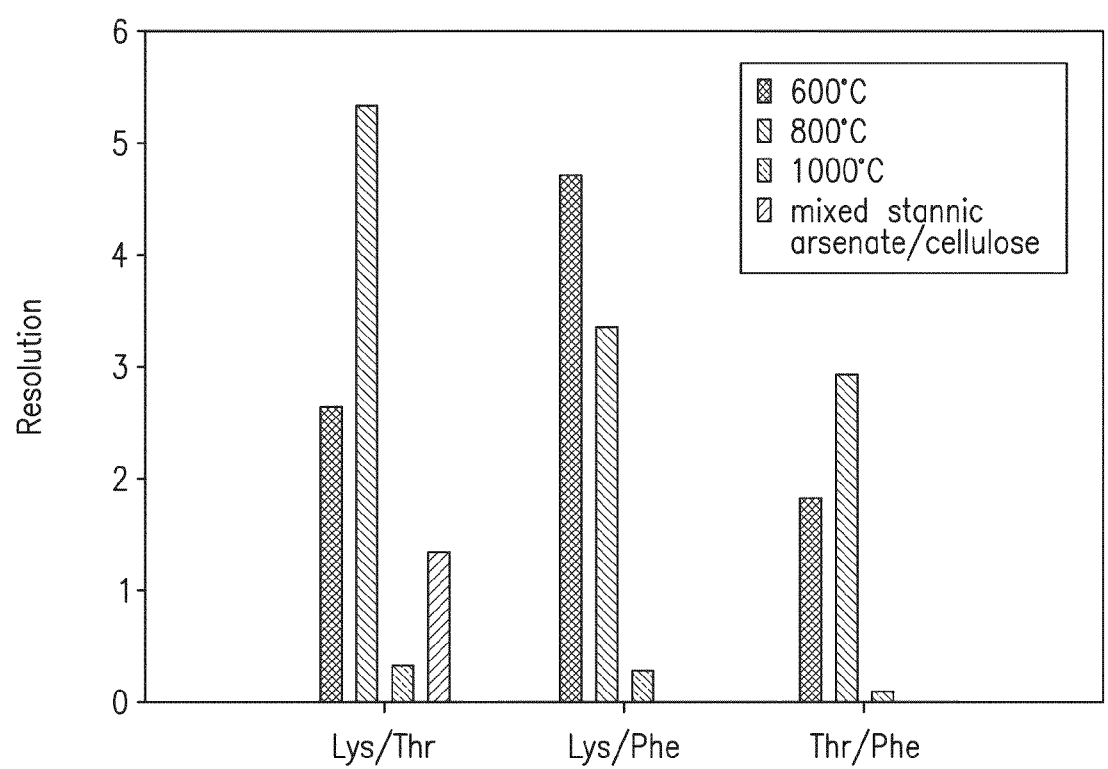
FIG. 34 is a graphical representation of the resolution of a ternary mixture of 3 essential amino acids: lysine, threonine and phenylalanine.

FIG. 34 demonstrates the resolution of separations performed with the electrospun glassy carbon UTLC devices and a comparison to previously published literature values. As was the case with the separation of laser dye mixtures, increasing the processing temperature (from 600-800° C. in this case) increases selectivity which results in higher resolution analyses. 600 and 800° C. devices showed the most desirable chromatographic performance for high efficiency separations of the ternary essential amino acid mixture. The electrospun carbon UTLC provides much higher N and resolution when compared to previous analyses. The results suggest that the mixture could be completely resolved at even shorter analysis times and development distances.

Electrospun glassy carbon nanofibrous stationary phases for UTLC were developed. This technique showed very high plate numbers (10,000s to 100,000s) and differing selectivity for the analysis of a set of 6 laser dyes as well as complete resolution of ternary mixtures of laser dyes and essential amino acids. Developed spot widths were similar to initial sample spot sizes, demonstrating that band broadening is very small using this technique. The selectivity of the devices can be tuned by pyrolyzing the electrospun nanofibers at different temperatures. The experimental results are in agreement with data obtained using Raman spectroscopy which shows an increase in the $sp^2$-character of the carbon material with increasing pyrolysis temperature leading to more conjugation, stronger π-π interactions and higher polarizability. The most strongly retained compounds were highly aromatic or charged compounds which were able to interact strongly with the glassy carbon stationary phase via multiple interaction modes. The described technique allows for the fabrication and use of a nanofibrous carbon stationary phase for UTLC which is chemically and mechanically robust and was found to have outstanding chromatographic performance.

While the invention has been described in connection with what is presently considered to be the most practical and preferred embodiments, it is to be understood that the invention is not to be limited to the disclosed embodiment(s), but on the contrary, is intended to cover various modifications and equivalent arrangements included within the spirit and scope of the appended claims, which are incorporated herein by reference.

What is claimed is:

1. A device for analytically separating chemical species, comprising:
    a solid phase micro extraction fiber, including:
        a conductive filament substrate;
        a coating of high contrast photoresist nanofibers electrospun on the surface of the conductive filament substrate, said coating having an average thickness of between 21.1 µm and 3.5 µM.

2. The device of claim 1, wherein said photoresist nanofibers are selectively cross-linked.

3. The device of claim 2, wherein at least a portion of the photoresist nanofibers are pyrolyzed forming carbon nanofibers.

4. The device of claim 3, wherein the at least a portion of the photoresist nanofibers are pyrolyzed at a temperature of about 400° C.

5. The device of claim 4, wherein the thickness of the photoresist nanofibers coating is about 11.4±1.0 µm.

6. The device of claim 3, wherein the at least a portion of the photoresist nanofibers are pyrolyzed at a temperature of about 600° C.

7. The device of claim 6, wherein the thickness of the photoresist nanofibers coating is about 6.2±0.7 µm.

8. The device of claim 7, wherein said solid phase micro extraction fiber has a detection limit of benzene of about 0.3 ng/ml and a detection limit of ethylbenzene of about 0.9 ng/ml and a linear range of about 0.05-40 µm/ml.

9. The device of claim 3, wherein the at least a portion of the photoresist nanofibers are pyrolyzed at a temperature of about 800° C.

10. The device of claim 9, wherein the thickness of the photoresist nanofibers coating is about 3.7±0.2 µm.

11. The device of claim 10, wherein said solid phase micro extraction fiber has a detection limit of benzene of about 0.4 ng/ml and a detection limit of ethylbenzene of about 1 ng/ml and a linear range of about 0.05-40 µm/ml.

12. The device of claim 1, wherein the photoresist nanofibers are devoid of binder material.

13. The device of claim 1, wherein photoresist nanofibers have an average diameter of about 301 nm.

14. The device of claim 1, wherein the conductive filament substrate is a stainless steel wire.

* * * * *

UNITED STATES PATENT AND TRADEMARK OFFICE
CERTIFICATE OF CORRECTION

PATENT NO. : 8,568,587 B2  
APPLICATION NO. : 13/046552  
DATED : October 29, 2013  
INVENTOR(S) : Olesik et al.

Page 1 of 1

It is certified that error appears in the above-identified patent and that said Letters Patent is hereby corrected as shown below:

In the Specification

Please delete:
"STATEMENT REGARDING FEDERALLY-SPONSORED R & D
The present invention was made with Government support under at least one of the following grants awarded by the National Science Foundation: 0616709, EEC-04-25626, and CHE-04-40499. The United States Government may have certain rights to this invention under 35 U.S.C. §200 et seq."

Please add:
"STATEMENT REGARDING FEDERALLY SPONSORED RESEARCH OR DEVELOPMENT
This invention was made with government support under grant numbers EEC0425626, CHE0440499 awarded by the National Science Foundation. The government has certain rights in the invention."

Signed and Sealed this  
Sixth Day of October, 2020

Andrei Iancu  
*Director of the United States Patent and Trademark Office*